US007795223B2

(12) United States Patent
Enk et al.

(10) Patent No.: US 7,795,223 B2
(45) Date of Patent: Sep. 14, 2010

(54) TREATMENT OF INFLAMMATORY AIRWAY DISEASE

(75) Inventors: Alexander Enk, Heidelberg (DE); Karsten Mahnke, Mainz (DE)

(73) Assignee: Novozymes Biopharma Au Ltd., Thebarton Sa (AU)

( * ) Notice: Subject to any disclaimer, the term of this patent is extended or adjusted under 35 U.S.C. 154(b) by 203 days.

(21) Appl. No.: 11/597,320

(22) PCT Filed: May 27, 2005

(86) PCT No.: PCT/AU2005/000762

§ 371 (c)(1),
(2), (4) Date: Dec. 28, 2006

(87) PCT Pub. No.: WO2005/115430

PCT Pub. Date: Dec. 8, 2005

(65) Prior Publication Data

US 2008/0200394 A1    Aug. 21, 2008

Related U.S. Application Data

(60) Provisional application No. 60/574,592, filed on May 27, 2004.

(51) Int. Cl.
*A61K 38/08* (2006.01)
*C07K 7/06* (2006.01)

(52) U.S. Cl. ............... 514/15; 514/16; 530/327; 530/328; 530/329; 530/345

(58) Field of Classification Search .................. None
See application file for complete search history.

(56) References Cited

U.S. PATENT DOCUMENTS

| 5,189,147 | A  | 2/1993 | Saito et al. |
| 6,057,294 | A  | 5/2000 | Manolios |
| 6,696,545 | B1 | 2/2004 | Buelow et al. |
| 6,713,606 | B1 | 3/2004 | Smith et al. |

(Continued)

FOREIGN PATENT DOCUMENTS

WO       WO 96/22306       7/1996

(Continued)

OTHER PUBLICATIONS

Gropep Press Release (2003).

(Continued)

*Primary Examiner*—Jeffrey E Russel
(74) *Attorney, Agent, or Firm*—Perkins Coie LLP

(57) ABSTRACT

This invention relates to methods of treatment of inflammatory airway disease, and in particular to methods of treatment of asthma and chronic obstructive pulmonary disease. The invention is applicable to both allergic (atopic) and non-allergic (intrinsic) asthma. In one form the method comprises the step of administering an effective amount of a compound which has the ability to inhibit one or more functions of the T cell receptor (TCR) to a subject in need of such treatment, which is preferably a peptide whose sequence is derived from an invariant region of (a) the $TCR_\alpha$ transmembrane domain; (b) the $TCR_\beta$ transmembrane domain; (c) the $TCR_\alpha$ intracellular domain; or (d) the CD3-$\gamma$, -$\delta$, -$\epsilon$, $\eta$ or $\xi$ chain.

32 Claims, 8 Drawing Sheets

Airway Resistance in asthmatic mice.

U.S. PATENT DOCUMENTS

2006/0110408 A1* 5/2006 Becker et al. ............ 424/234.1
2007/0160631 A1* 7/2007 Jackson et al. ............ 424/209.1

FOREIGN PATENT DOCUMENTS

| WO | WO 97/43411 A1 | 11/1997 |
|---|---|---|
| WO | WO 97/47644 | 12/1997 |
| WO | WO 98/02454 | 1/1998 |
| WO | WO 01/43695 A2 | 6/2001 |
| WO | WO 02/080967 A1 | 10/2002 |
| WO | WO 03/060097 A2 | 7/2003 |

OTHER PUBLICATIONS

GroPep Annual Report, 2003 (p. 13).

M. Ali et al., "Peptide Delivery Systems", Letters in Peptide Science, 8: pp. 289-294, 2002.

Richard S. Blumberg et al., "Assembly and Function of the T Cell Antigen Receptor", The Journal of Biological Chemistry, vol. 265, No. 23, Issue of Aug. 15, pp. 14036-14043, 1990.

M. Ali et al., "Biophysical Studies of a Transmembrane Peptide Derived From the T Cell Antigen Receptor", Letters in Peptide Science, 8: 227-233, 2002.

GP Goellner et al., "Therapeutic Application of T Cell Receptor Mimic Peptides or CDNA in the Treatment of T Cell-Mediated Skin Diseases", Gene Therapy, (2000), 7, pp. 1000-1004.

Alexander Enk et al., "T Cell Receptor Mimic Peptides and Their Potential Application in T-Cell-Mediated Disease," International Archives of Allergy and Immunology, 2000, 123:275-281.

Nicholas Manolios et al., "Transmembrane Helical Interactions and the Assembly of the T Cell Receptor Complex", Science, vol. 249, pp. 274-277 (1990).

Marina Ali et al., "Photoactive Benzophenone Labelled Peptide", Journal of Rheumocology, 7:11-12, 2004.

Zhanguo Li et al., "The Interchain Disulfide Linkage of T-Cell Antigen Receptor—$\alpha$ and—$\beta$ Chains is a Prerequisite for T-Cell Activation", Cellular Immunology, 190: 101-111, 1998.

Nghi T. Huynh et al., Transmembrane T-Cell Receptor Peptides Inhibit B- and Natural Killer-Cell Function, Immunology, 2003, 108: 458-464.

Xin M. Wang et al., "T Cell Antigen Receptor (TCR) Transmembrane Peptides Colocalize with TCR, not Lipid Rafts, in Surface Membranes", Cellular Immunology, 215 (2002) 12-19.

Zhanguo Li et al., "Structural Mutations in the Constant Region of the T-Cell Antigen Receptor (TCR) $\beta$ Chain and Their Effect on TCR$\alpha$ and $\beta$ Chain Interaction", Immunology, 88: 524-530, 1996.

Xin M. Wang et al., "T-Cell Antigen Receptor Peptides Inhibit Signal Transduction Within the Membrane Bilayer", Clinical Immunology, vol. 105, No. 2, November, pp. 199-207 (2002).

Mahnke, et al., "Dendritic cells, engineered to . . . immunosuppression in vivo", Nature Biotechnology, Aug. 2003, pp. 903-908, vol. 21, No. 8.

Lisbonne, et al., "Cutting Edge: Invariant Va14 Nkt . . . Experimental Asthma Model", Journal of Immunology, 2003, pp. 1637-1641.

Enk, et al., "T Cell Receptor Mimic Peptides . . . T-Cell-Mediated Disease", Allergy and Immunology, 2000, pp. 275-281, vol. 123.

Manolios, et al., "T-cell antigen receptor . . . and T cell-mediated disease", Nature Medicine, pp. 84-88, vol. 3, (1997).

* cited by examiner

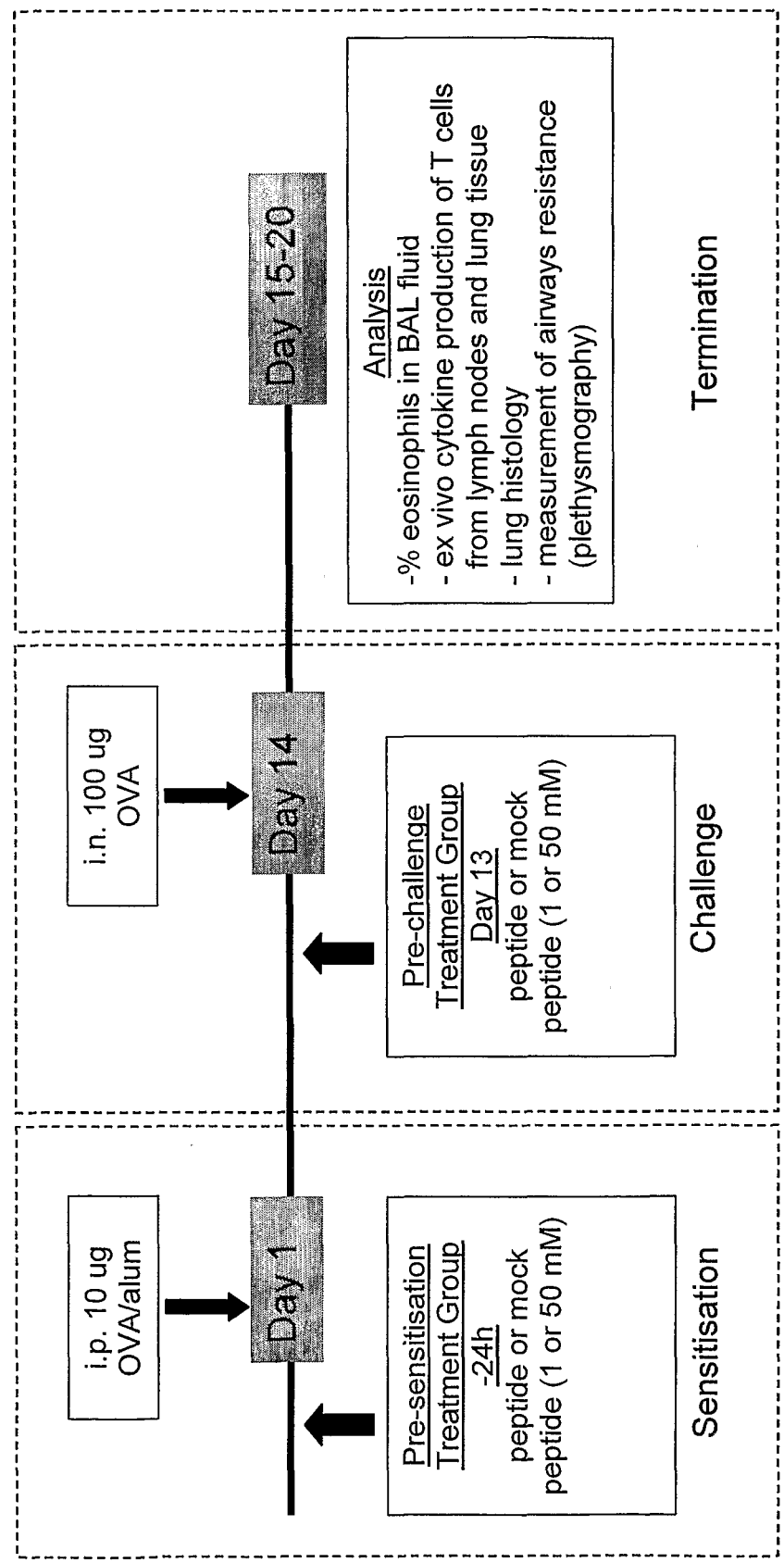
Figure 1. Allergen (OVA)-induced asthma in a mouse model

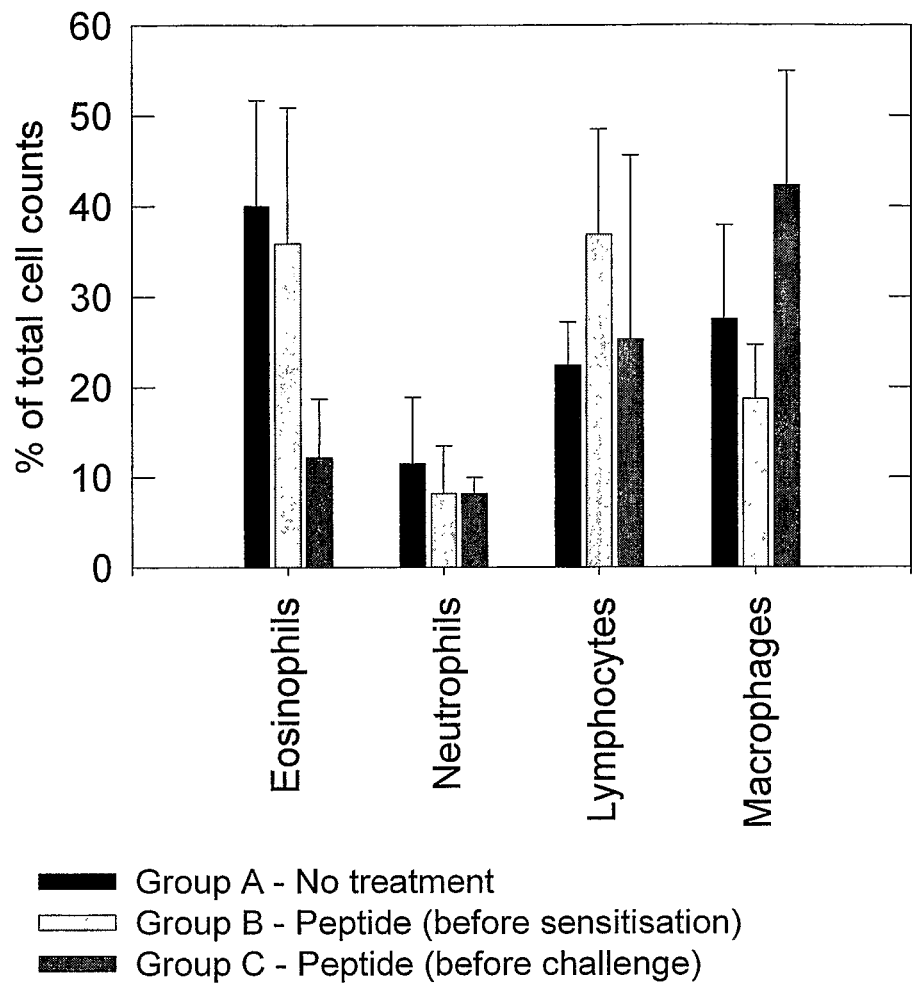
Figure 2. Total and differential cell counts in BAL fluid from asthmatic mice 3 days after antigen challenge.

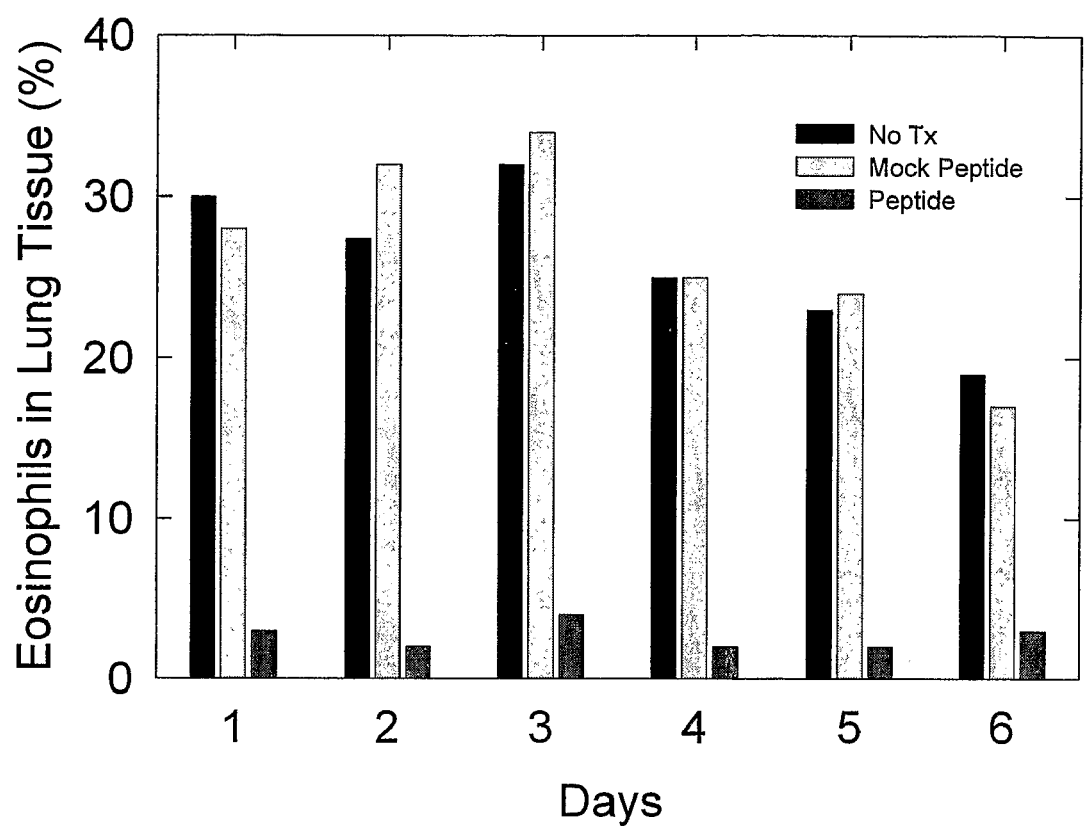
Figure 3. Infiltration of eosinophils in lung tissue .

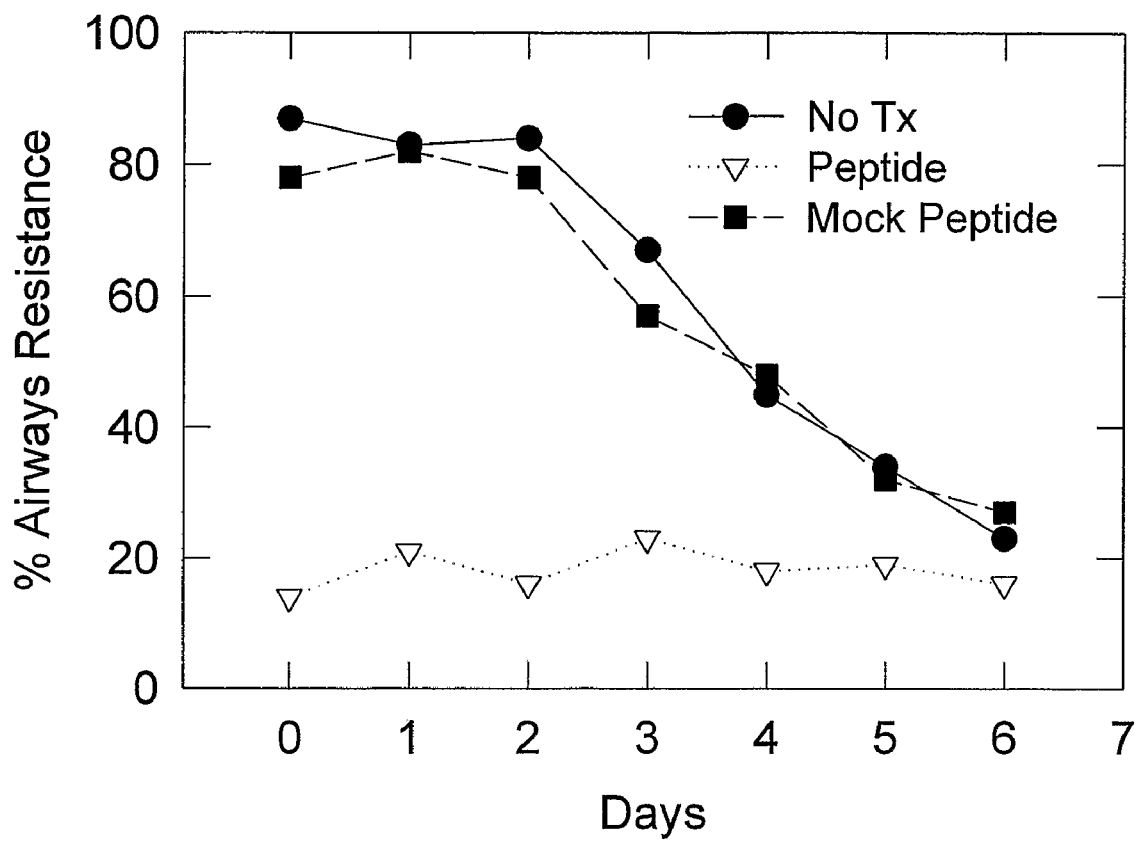
Figure 4. Airway Resistance in asthmatic mice.

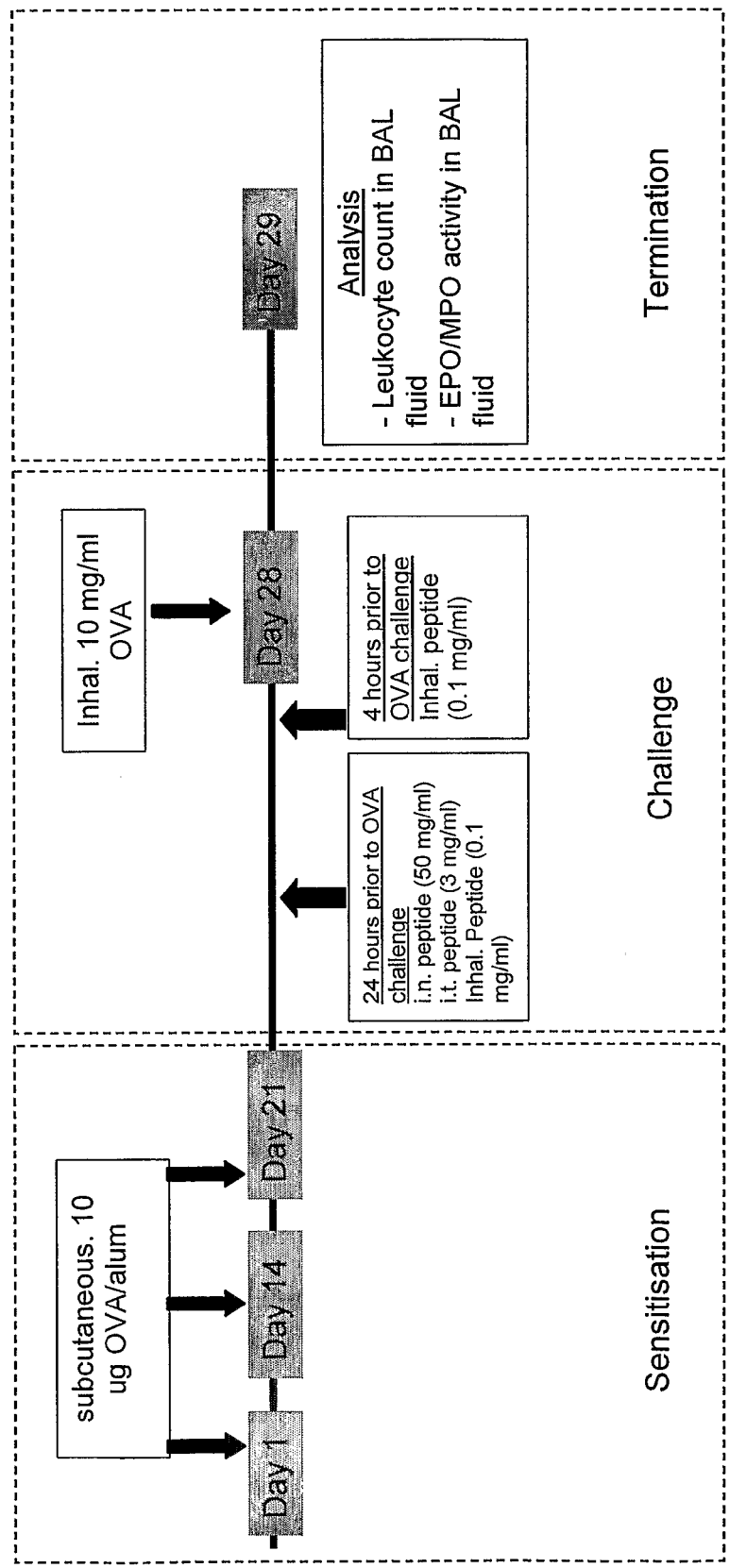
Figure 5. Allergen (OVA)-induced Eosinophilia in a rat

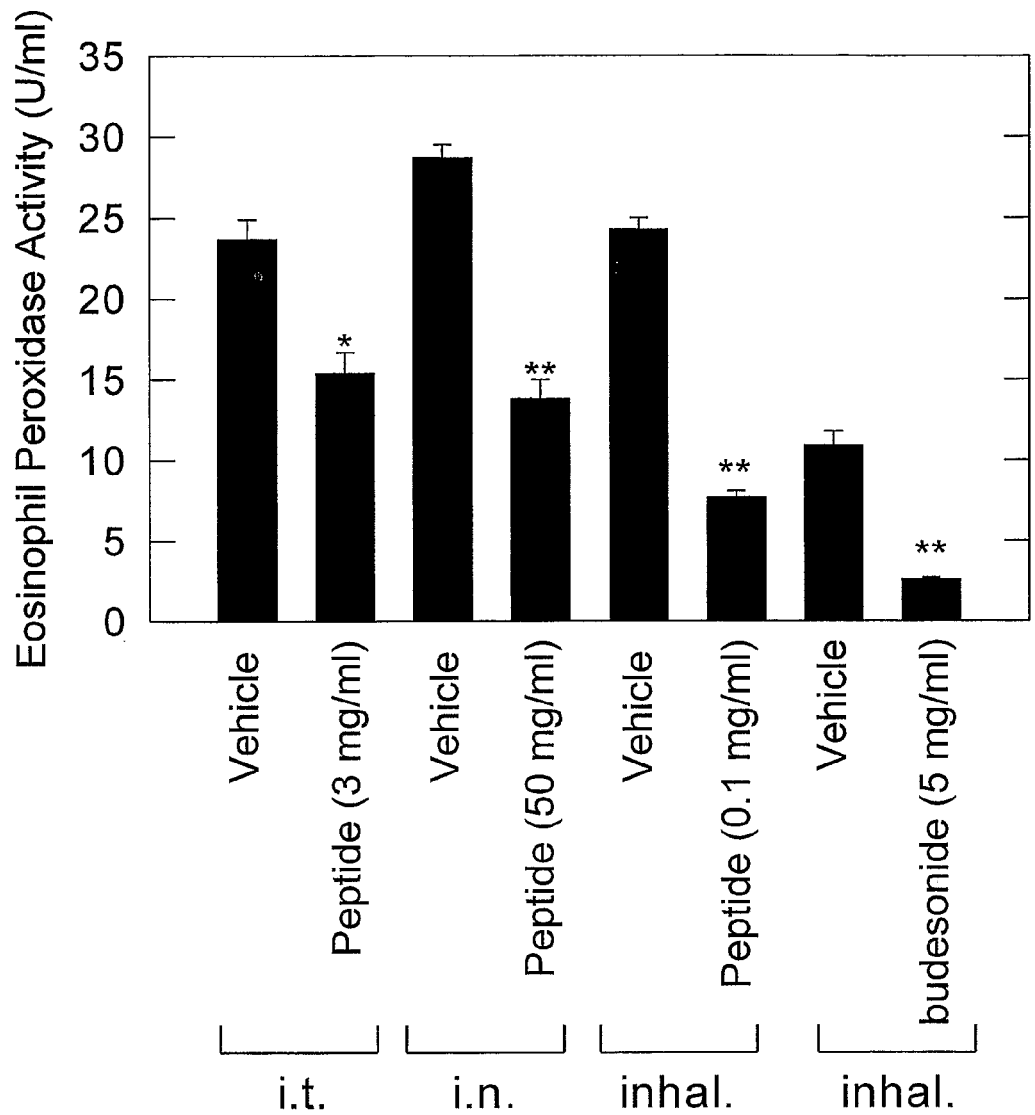
Figure 6. Eosinophil Peroxidase activity in BAL fluid

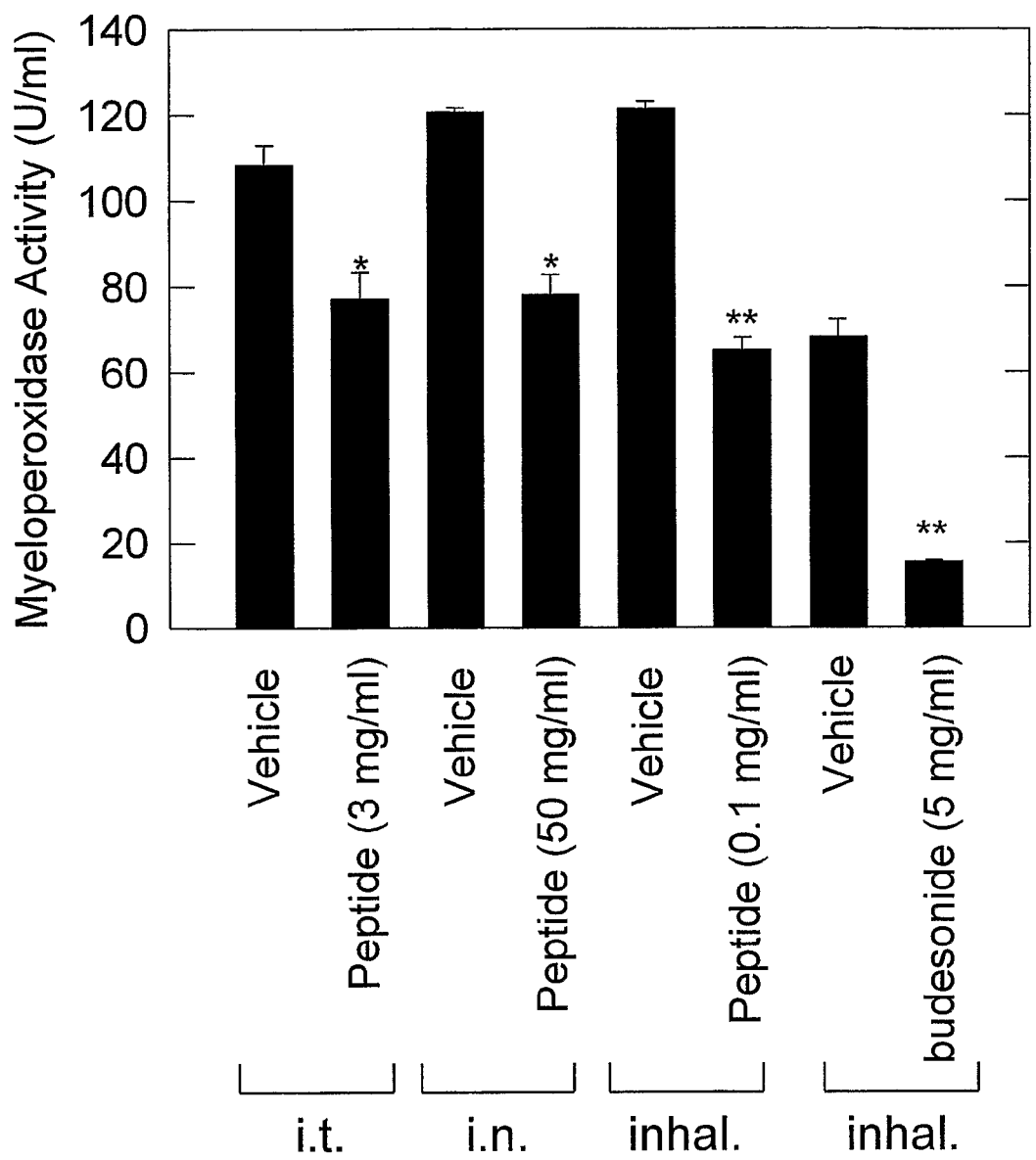
Figure 7. Myeloperoxidase activity in BAL fluid

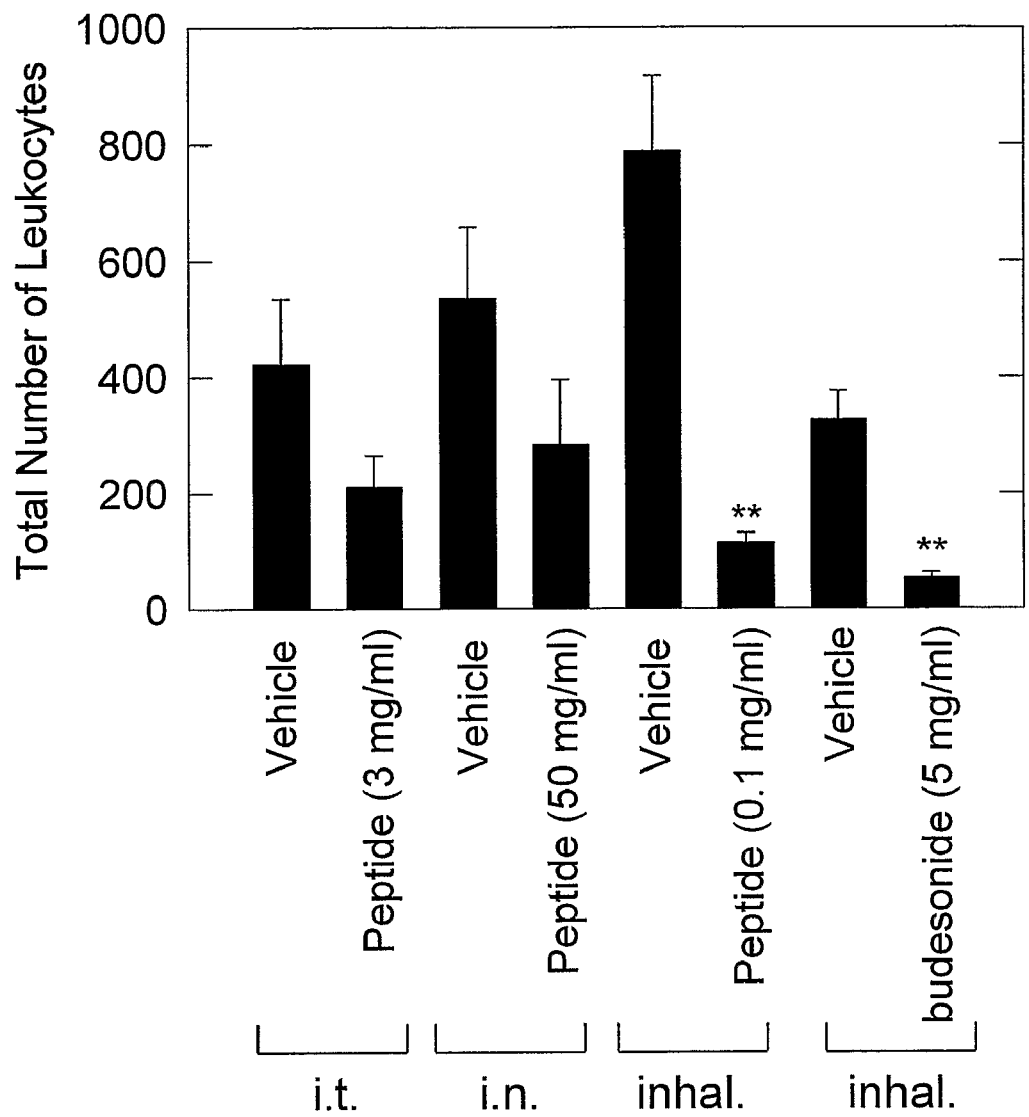
Figure 8. Total number of leukocytes recovered from BAL fluid

TREATMENT OF INFLAMMATORY AIRWAY DISEASE

This application claims priority from U.S. provisional patent application No. 60/574,592 dated 27 May 2004, the entire contents of which are incorporated herein by this reference.

FIELD

This invention relates to methods of treatment of inflammatory airway disease, and in particular to methods of treatment of asthma and chronic obstructive pulmonary disease. The invention is applicable to both allergic (atopic) and non-allergic (intrinsic) asthma.

BACKGROUND

It will be clearly understood that, although a number of prior art publications are referred to herein to describe background information, this reference does not constitute an admission that any of these documents forms part of the common general knowledge in the art, in Australia or in any other country. The discussion of the references states what their authors assert, and the applicants reserve the right to challenge the accuracy and pertinency of the cited documents.

Some references are made in the detailed description to documents that describe certain features of the present invention. Such references, including patents or patent applications, are hereby incorporated by reference.

Asthma is a chronic disease characterized by intermittent, reversible, widespread constriction of the airways of the lungs in response to any of a variety of stimuli which do not affect the normal lung. There is chronic inflammation and paradoxical narrowing of the bronchi, and recurrent acute episodes of limited airflow, mucus production and cough. The symptoms, which are provoked by allergens such as pollens, mould spores, pet or other animal danders and house dust mites, or by environmental triggers such as tobacco smoke or other air pollutants, include wheezing, shortness of breath, difficulty in breathing, especially on exhalation, and tightness of the chest. Other triggers include infections such as colds and other upper respiratory infections, viruses or sinus infections, irritants such as strong odours from perfumes or cleaning solutions, exercise or exertion, changes in temperature or humidity, stress and strong emotion. Asthma which is provoked by allergens is generally known as allergic asthma or atopic asthma.

Type 1 (immediate) immune responses may play an important role in the development of asthma in children and many adults; however, when the onset of disease occurs in adulthood, allergic factors may be difficult to identify.

Thus asthma is broadly divided into two types: extrinsic asthma, which is also known as allergic or atopic asthma, and intrinsic or non-atopic asthma. These two subclasses of asthma are referred to herein as allergic and non-allergic asthma respectively. The immunopathology of these two forms of asthma has been reviewed by Humbert M. et al. 1999. Allergic asthma is characterised by infiltration of eosinophils and T helper 2 (Th2)-type cells into the bronchial mucosa, the presence of specific immunoglobulin E (IgE) antibodies in the circulation, positive skin test reactions to common airborne allergens, and airway hyper-responsiveness. Synthesis of IgE by B cells is believed to be stimulated by interleukin-4 (IL-4), and mobilisation of eosinophils is believed to be stimulated by interleukin-5 (IL-5). In contrast to this, patients suffering from non-allergic asthma have negative skin tests, and have no clinical or family history of allergy, and they have no specific IgE antibodies directed against common allergens. Moreover, these patients are usually older than those with allergic asthma, and their symptoms first present in later life; they often manifest a more severe clinical course.

Studies on bronchial biopsy samples showed that both forms of asthma were characterised by infiltration of eosinophils and Th2 cells secreting IL-4, IL-5 or both of these cytokines; the presence of CC chemokines and $Fc\epsilon RI^+$ cells; and cells which express mRNA for the $\epsilon$ germ-line transcript (I$\epsilon$) and the $\epsilon$ heavy chain of IgE (C$\epsilon$). The only apparent difference was a marked elevation in $CD68^+$ macrophages expressing the GM-CSF receptor $\alpha$ subunit in patients with non-allergic asthma, compared with those suffering from allergic asthma (Humbert M. et al. 1999). Since both T cells and B cells are implicated in asthmatic responses, particularly in the production of IgE, modulation of both T and B cell responses would be expected to be useful in the treatment of extrinsic and intrinsic asthma.

Asthma affects 12-15 million Americans, including approximately 10%-12% of children under the age of 18. Between about 10% and 33% of all patients with asthma have the non-allergic form. People who have a family history of asthma have an increased risk of developing the disease. Asthma is also more common in people who have allergies or who are exposed to tobacco smoke. Asthma often develops in childhood or the teenage years, and is the most common chronic childhood disease. Although it is more common in individuals under 40 years old, asthma can develop at any age.

Treatment of asthma focuses on the use of medications which control inflammation and prevent chronic symptoms (long-term control medications) and medications which treat asthma attacks when they occur (quick relief medications), and avoiding asthma triggers. There are two general types of asthma medications:

(a) Anti-inflammatory drugs, which prevent asthma attacks on an ongoing basis. Steroids, also called "corticosteroids," are an important type of anti-inflammatory medication for people suffering from asthma. These drugs reduce swelling and mucus production in the airways. As a result, the airways are less sensitive and less likely to react to triggers.

(b) Bronchodilators, which relieve the symptoms of asthma by relaxing the muscle bands that tighten around the airways. This action rapidly opens the airways, letting more air to enter and leave the lungs. As a result, breathing improves. Bronchodilators also help to clear mucus from the lungs. As the airways open, the mucus moves more freely and can be coughed out more easily.

In addition to these conventional medications, a recombinant humanized monoclonal antibody against IgE (Xolair; Genentech, Inc), was approved in June 2003. This antibody blocks binding of IgE to mast cells and basophils, thus inhibiting the allergic reaction which causes constriction of the airways.

Preventing the inflammation is the key to preventing asthma attacks, hospitalizations and death from asthma. Long-term control medications are taken daily over an extended period of time to achieve and maintain control of persistent asthma, ie asthma which causes symptoms more than twice a week and frequent attacks which affect activity.

The most effective long-term control medications are anti-inflammatory drugs, but there are others which are often used along with anti-inflammatory drugs to enhance their effect. These medications include:

1. Corticosteroids: the inhaled form is the anti-inflammatory drug of choice for persistent asthma;

2. Mast cell stabilizers: anti-inflammatory drugs;

3. Long acting β-agonists: bronchodilators often used along with an anti-inflammatory drug;

4. Theophylline: a bronchodilator used along with anti-inflammatory to prevent nighttime symptoms; and 5. Leukotriene modifiers: an alternative to steroids and mast cell stabilizers.

Despite the availability of all these medications, asthma is frequently very difficult to control, and each year acute asthma attacks (status asthmaticus) result in frequent hospital admissions, especially among children, and in a significant number of deaths.

Asthma is regarded as being a quite different condition from allergic alveolitis, which is also known as extrinsic allergic alveolitis, allergic interstitial pneumonitis, extrinsic allergic pneumonia or hypersensitivity pneumonitis. Extrinsic allergic alveolitis is a relatively rare lung disorder resulting from repeated inhalation of organic dust, usually in a specific occupational setting. In the acute form, respiratory symptoms and fever begin several hours after exposure to the dust. The chronic form is characterized by gradual changes in the lung tissue associated with several years of exposure to the irritant. It has been variously named bagassosis, bathtub refinisher's lung, bird or pigeon breeder's disease, cheese worker's lung, enzyme detergent sensitivity, epoxy resin lung, farmer's lung, laboratory technician's lung, maltworker's lung, maple bark-stripper's disease, mushroom picker's disease, mushroom worker's lung, snuff-taker's lung, plastic worker's lung, poultry breeder's disease, sequoiosis, suberosis, ventilation pneumonitis, and wheat weevil disease, depending on the initiating agent.

Chronic obstructive pulmonary disease (COPD), also known as chronic obstructive lung disease (COLD) or chronic airflow obstruction (CAO), is a group of diseases principally consisting of emphysema, obliterative bronchiolitis and chronic bronchitis. COPD is the fourth leading cause of death in the United States, and is a leading cause of disability. Approximately 15 million Americans are affected by COPD, and there is an increasing incidence in women. COPD is a chronic progressive disease process which most commonly results from smoking, but may also be provoked by prolonged exposure to other lung irritants such as industrial dust or chemical fumes. Genetic factors, low birth weight or repeated lung infections may increase susceptibility to COPD. COPD develops over a long period, sometimes as much as 10 to 30 years, and is most commonly diagnosed at the age of 60 or greater. Consequently COPD is generally regarded as a disease of older adults. COPD is characterised by difficulty in breathing, wheezing and a chronic cough. Treatment includes absolute avoidance of smoking, with the use of bronchodilators and oxygen for those with advanced disease, and emphysema patients may undergo surgery to reduce lung volume. COPD patients are subject to periodic exacerbations of the condition which result in a rapid increase in shortness of breath, which may be life-threatening.

Chronic bronchitis (CB) is inflammation of one or more bronchi, usually secondary to infection, and is characterized by excessive production of mucus in the bronchi, accompanied by a recurrent cough which persists for at least three months of the year during at least two successive years. CB is the major non-asthmatic disease of the lung. Many different factors initiate CB, including cigarette smoking, environmental pollution, chronic infections and various genetic abnormalities. Of these factors, cigarette smoking is the most prevalent. Pathological changes in the lung include:

(1) hypertrophy and hyperplasia of mucus-secreting glands in the bronchi, (2) increase in goblet cells, (3) disappearance or damage of cilia, and (4) chronic inflammatory changes and narrowing of small airways.

A bacterial or viral infection is often present. Excess amounts of mucus are found in the airways, and sometimes may occlude small bronchioles. Eventually there may be scarring of the bronchial wall. Coughing is stimulated by retained mucus, which cannot be adequately removed due to decreased cilia and lessened mucociliary clearance (Svartengren et al. 1996). It is important that bronchitis patients clear retained mucus by coughing; however, often coughing is ineffective in adequately removing these secretions because the bronchitis patient cannot inspire deeply enough to cause air to flow distal to retained secretions.

Emphysema is a lung condition which results from damage to the alveolar sacs in the lungs, usually caused by long-term smoking. This damage leads to a pathological accumulation of air in the tissues.

The reduction of chronic inflammation by the inhibition of T-cell and B-cell function in emphysema, obliterative bronchiolitis and chronic bronchitis, and consequent reduction in the narrowing of small airways in patients suffering from these conditions, would greatly reduce the burden on the health system caused by these common debilitating diseases.

The T cell receptor (TCR) is composed of at least seven transmembrane proteins. The disulphide-linked (αβ-Ti) heterodimer forms the clonotypic antigen recognition unit, while the invariant chains of CD3, consisting of γ, δ, ε, ζ and η chains, are responsible for coupling the ligand binding to signalling pathways which result in T-cell activation and the elaboration of the cellular immune responses. Despite the diversity of the genes encoding the TCR polypeptide chains, two structural features are common to all known TCR subunits. Firstly, they are transmembrane proteins with a single transmembrane spanning domain, which is presumably α-helical. Secondly, all the TCR chains share the unusual feature of possessing a charged amino acid within the predicted transmembrane domain. The invariant chains have a single negative charge, conserved between the mouse and human, and the variant chains possess one (TCRβ) or two (TCRα) positive charges.

International patent applications No. PCT/AU96/00018 and No. PCT/AU97/00367 by Northern Sydney Area Health Services disclose peptides which are able to inhibit the function of the mammalian T-cell receptor for antigen (TCR). The entire contents of these two documents are incorporated herein by this reference. These peptides were designed on the basis of the discovery that the stable interaction between the TCR-α chain and the CD3-δ and CD3-ε subunits was localised to 8 amino acids within the transmembrane domain of TCR-α, and that charged amino acids were critical for this interaction, as disclosed in PCT/AU96/00018. Additional peptides were based on sequences from peptides corresponding to alternative chain assembly regions in the CD3-δ, -ε and -γ chains, the TCR-αβ interchain disulphide bond interaction region, and regions downstream of the core peptide (GFRILLLKV (SEQ ID NO: 26) (human) or GLRILLLKV (SEQ ID NO: 27) (murine)). These are disclosed in PCT/AU97/00367. These peptides were shown to be able to penetrate into cells, and to decrease the symptoms of T cell-mediated inflammation in vivo in the adjuvant-induced arthritis model in rats. The results were also reported in the literature (Manolios et al. 1997). The entire contents of this document are incorporated herein by this reference.

It was proposed that the peptides would be useful in the treatment of a variety of disorders in which T cells are involved or in which T cells are recruited to the site of the pathology, including rheumatoid arthritis. One of these peptides, corresponding to a 9-amino acid region in the transmembrane domain of the TCR-α chain, can suppress T cell function both in vitro and in vivo, and inhibits production of interleukin-2 following antigen-induced stimulation Rang et al. 2002). It has also been demonstrated that a 9-amino acid peptide, Gly-Leu-Arg-Ile-Leu-Leu-Leu-Lys-Val (SEQ ID NO: 1), designated "core peptide", inhibited development of contact sensitivity when applied topically following application of a contact allergen in sensitised animals (Enk and Knop 2000; Gollner et al 2000; Manolios et al. 2002). Enk and Knop and Gollner et al. also showed that subcutaneous injection of naked DNA encoding the peptide sequence prior to application of the contact allergen prevented development of contact sensitivity. The peptide showed therapeutic activity in human patients with psoriasis, atopic eczema, lichen planus, or contact dermatitis, and they concluded that the peptide, or DNA encoding it, would be useful as an alternative to corticosteroids in treatment of human T cell-mediated dermatoses.

SUMMARY

We have now found that administration of a TCR mimic peptide prior to challenge with allergen resulted in a marked reduction of leukocyte and eosinophil infiltration into lung tissue, particularly eosinophils, and a reduction in eosinophil peroxidase and myeloperoxidase activity in bronchoalveolar lavage fluid, as well as a significant reduction in obstruction of the airways as measured by whole body plethysmography.

In a first aspect, the invention provides a method of treatment of inflammatory airway or lung disease, comprising the step of administering an effective amount of a peptide which has the ability to inhibit one or more functions of the T cell receptor (TCR) to a subject, in which the peptide has a sequence derived from an invariant region of
   (a) the $TCR_\alpha$ transmembrane domain;
   (b) the $TCR_\beta$ transmembrane domain;
   (c) the $TCR_\alpha$ intracellular domain; or
   (d) the CD3-γ, -δ, -ε, η or ξ chain.

In one embodiment, the compound is a peptide which has the ability to inhibit the formation of the TCR complex from its subunits.

In one form of this aspect of the invention, the peptide has the formula A-B-C-D-E, in which
   A is absent, or is glycine and 1 hydrophobic amino acid, or is 1 or 2 hydrophobic amino acids;
   B is a positively charged amino acid;
   C is a peptide consisting of 1, 2, 3, 4 or 5 hydrophobic amino acids;
   D is a positively-charged amino acid; and
   E is absent, or is 1, 2, 3, 4, 5, 6, 7 or 8 hydrophobic amino acids.

In one embodiment of this form of the invention, C is a peptide consisting of 3, 4 or 5 hydrophobic amino acids, preferably 3 or 4 hydrophobic amino acids, preferably 4 hydrophobic amino acids.

In a second embodiment, A is 2 hydrophobic amino acids and E is 1, 2 or 3 hydrophobic amino acids, more preferably one hydrophobic amino acid.

In a third embodiment,
   (a) B is arginine and D is lysine, or
   (b) B is lysine and D is arginine.

In a fourth embodiment, E is a peptide consisting of 1, 2, 3, 4, 5, 6, 7 or 8 amino acids.

In a fifth embodiment, the peptide is $NH_2$-Gly-Leu-Arg-Ile-Leu-Leu-Leu-Lys-Val-OH (SEQ.ID.NO.:1);

$NH_2$-Leu-Lys-Ile-Leu-Leu-Leu-Arg-Val-OH (SEQ.ID.NO.:2);

$NH_2$-Gly-Phe-Arg-Ile-Leu-Leu-Leu-Lys-Val-OH (SEQ.ID.NO.:3);

$NH_2$-Val-Phe-Arg-Ile-Leu-Leu-Leu-Lys-Val-OH (SEQ.ID.NO.:4);

$NH_2$-Phe-Lys-Ile-Leu-Leu-Leu-Arg-Val-OH (SEQ.ID.NO.:5);

$NH_2$-Ala-Arg-Leu-Pro-Val-Leu-Lys-Leu-Val-OH (SEQ.ID.NO.:6);

$NH_2$-Arg-Val-Met-Ala-Pro-Arg-Ala-Leu-Leu-OH (SEQ.ID.NO.:7);

$NH_2$-Val-Lys-Leu-Phe-Pro-Val-Lys-Leu-Phe-Pro-OH (SEQ.ID.NO.:8);

$NH_2$-Leu-Arg-Ile-Leu-Leu-Leu-Ile-Lys-Val-OH (SEQ.ID.NO.:9); or $NH_2$-Leu-Arg-Leu-Leu-Leu-Lys-Val-OH (SEQ.ID.NO.:10).

Preferably in this embodiment the peptide is Gly-Leu-Arg-Ile-Leu-Leu-Leu-Lys-Val (SEQ ID NO: 28).

In a second form of this aspect of the invention, the compound is a peptide of the formula $NH_2$—P-Q-P—COOH, in which P is a hydrophobic amino acid or a hydrophobic peptide of 2, 3, 4, 5, 6, 7, 8, 9, 10, 11 or 12 amino acids, and
   Q is a charged amino acid.

In specific embodiments of this form of the invention,
   (a) P is a hydrophobic amino acid or a hydrophobic peptide sequence consisting of 2, 3, 4, 5 or 6 amino acids;
   (b) P includes at least one hydrophobic amino acid and does not include a charged amino acid, and preferably at least 50% of the amino acids make up the hydrophobic peptide are hydrophobic amino acids. More preferably at least 80% of the amino acids which make up the hydrophobic peptide are hydrophobic amino acids;
   (c) Where the peptide sequence is derived from the $TCR_\alpha$ transmembrane domain, Q is a positively charged amino acid, and is preferably lysine or arginine;
   (d) Where the peptide sequence is derived from the CD3-γ, -δ or -ε transmembrane domain, Q may be a negatively charged amino acid. Where the peptide sequence is derived from the CD3-δ or -ε domain, Q may be aspartic acid. Where the peptide sequence is derived from the CD3-γ domain, Q may be glutamic acid; and
   (e) The peptide comprises a cysteine residue, and has the ability to destabilize the interchain disulphide bond between the $TCR_\alpha$ and $TCR_\beta$ chains.

Preferably the peptide is selected from the group consisting of $NH_2$-Met-Gly-Leu-Arg-Ile-Leu-Leu-Leu-OH (SEQ.ID.NO.:11);

$NH_2$-Leu-Asp-Ile-Leu-Leu-Leu-Glu-Val-OH (SEQ.ID.NO.:12);

$NH_2$-Ile-Leu-Leu-Leu-Lys-Val-Ala-Gly-Phe-OH (SEQ.ID.NO.:13);

NH$_2$-Ile-Leu-Leu-Leu-Lys-Val-Ala-Gly-OH (SEQ.ID.NO.: 14);

NH$_2$-Leu-Arg-Ile-Leu-Leu-Leu-Gly-Val-OH (SEQ.ID.NO.: 15);

NH$_2$-Leu-Gly-Ile-Leu-Leu-Leu-Lys-Val-OH (SEQ.ID.NO.: 16);

NH$_2$-Ile-Leu-Leu-Gly-Lys-Ala-Thr-Leu-Tyr-OH (SEQ.ID.NO.:17);

NH$_2$-Leu-Leu-Met-Thr-Leu-Arg-Leu-Trp-Ser-Ser-OH (SEQ.ID.NO.:18);

NH$_2$-Ile-Ile-Val-Thr-Asp-Val-Ile-Ala-Thr-Leu-OH (SEQ.ID.NO.:19);

NH$_2$-Ile-Val-Ile-Val-Asp-Ile-Cys-Ile-Thr-OH (SEQ.ID.NO.: 20);

NH$_2$-Phe-Leu-Phe-Ala-Glu-Ile-Val-Ser-Ile-OH (SEQ.ID.NO.:21);

NH$_2$-Tyr-Gly-Arg-Ala-Asp-Cys-Gly-Ile-Thr-Ser-OH (SEQ.ID.NO.:22);

NH$_2$-Trp-Gly-Arg-Ala-Asp-Cys-Gly-Ile-Thr-Ser-OH (SEQ.ID.NO.:23);

NH$_2$-Tyr-Gly-Arg-Ala-Asp-Cys-Ile-Thr-Ser-OH (SEQ.ID.NO.:24); and

NH$_2$-Ser-Ser-Asp-Val-Pro-Cys-Asp-Ala-Thr-Leu-Thr-OH (SEQ.ID.NO.:25).

More preferably the peptide is

```
                                          (SEQ ID NO: 15)
NH2-Leu-Arg-Ile-Leu-Leu-Leu-Gly-Val-OH, (SEQ ID NO: 18)
NH2-Leu-Leu-Met-Thr-Leu-Arg-Leu-Trp-Ser-Ser-OH
or
                                          (SEQ ID NO: 20)
NH2-Ile-Val-Ile-Val-Asp-Ile-Cys-Ile-Thr-OH.
```

In a third form of this aspect of the invention, the compound is a peptide of the formula NH$_2$—W—X—Y—COOH, in which W is absent, or is 1, 2, 3, 4 or 5 amino acids;

X is cysteine or a charged amino acid;

W is a peptide sequence of 2, 3, 4, 5, 6, 7, 8, 9 or 10 amino acids.

In one embodiment the peptide is derived from the TCR-β chain. Preferably Y is a peptide consisting of 4 or 5 amino acids, and includes at least one hydrophobic amino acid.

In a fourth form of this aspect of the invention,

W is an amino acid selected from the group consisting of alanine, isoleucine, leucine, valine, glycine, methionine, threonine, phenylalanine, tryptophan and serine, Y is an amino acid selected from the group consisting of glycine, alanine, valine, leucine, isoleucine, threonine, methionine, glutamine, asparagine, and cysteine, and X is a charged amino acid.

It was shown in PCT/AU96/00018 that there is complete sequence homology across a range of species in the last fifteen amino acids of the TCR-α chain distal to the sequence of the peptides specifically disclosed therein, and that peptides including these additional 15 residues may also possess anti-inflammatory activity. Moreover, modification of the peptide at the carboxy terminal, for example by conjugation with a lipid carrier, did not alter the function of the peptides.

Consequently in a second aspect the invention provides a method of treatment of an inflammatory lung disease, comprising the step of administering an effective amount of a peptide as defined above, in which either the C-terminal or the N-terminal of the peptide is chemically conjugated to a lipid moiety. The lipid moiety facilitates absorption and/or transfer across cell membranes.

In one embodiment the lipid moiety is a fatty acid of 2, 3, 4, 5, 6, 7, 8, 9, 10, 11, 12, 13, 14, 15, 16, 17, 18, 19, 20, 21, 22, 23, 24, 25, 26, 27, 28, 29 or 30 carbon atoms, which may be a saturated, monounsaturated or polyunsaturated fatty acid. Preferably the fatty acid is palmitoyl, myristoyl, stearoyl or decanoyl.

In an alternative embodiment the lipid moiety is a fatty acid coupled to tris(hydroxymethyl) amino methane (TRIS; also known as tromethamine) or ethanolamine; preferably the fatty acid has 3, 4, 5, 6, 7, 8, 9, 10, 11, 12, 13, 14, 15, 16, 17 or 18, more preferably 10, 11, 12, 13, 14, 15, 16, 17 or 18, most preferably 16 carbon atoms. In a particularly preferred embodiment the lipid moiety is TRIS(monopalmitate) or TRIS(tripalmitate).

Suitable TRIS-fatty acids and methods for their production are described in U.S. Pat. No. 5,583,198 and No. 5,869,606, and in Whittaker et al. 1993, the entire disclosures of which are incorporated herein by this reference.

In another alternative embodiment, the lipid moiety is N-palmitoyl-S-[2,3-bis(palmitoyloxy)propyl]cysteine (Pam$_3$Cys; Wiesmuller et al. 1983, or another N-acyl-S-(2-hydroxyalkyl) cysteine as described in U.S. Pat. No. 5,700,910, or is an analogue in which only two acyl substituents are present, such as S-[2,3-bis(palmitoyloxy)propyl]cysteine) Pam$_2$Cys; Metzger et al. 1995). The entire disclosures of these documents are incorporated herein by this reference.

The inflammatory airway or lung disease may be asthma, which is to be taken to include both allergic asthma and non-allergic asthma, or may be chronic obstructive pulmonary disease (COPD), which includes emphysema, chronic bronchitis and obliterative bronchiolitis.

In one embodiment, the inflammatory airway or lung disease is asthma. In a second embodiment the inflammatory airway or lung disease is COPD. In one form of the second embodiment, the compound reduces inflammation, and thereby reduces narrowing of the small airways. The emphysema may result from damage to the lungs, for example as a result of long-term smoking, or may be caused by congenital deficiency of α$_1$-antitrypsin.

It will be clearly understood that because both allergic asthma and non-allergic asthma are characterised by infiltration of eosinophils and IL-4 and IL-5-secreting Th2 cells into the bronchial mucosa, the invention encompasses both of the subclasses of asthma.

The peptide or peptide conjugate may be administered intravenously, subcutaneously, intratracheally, intrabronchially, intranasally or via inhalation. Preferably the peptide is administered via inhalation.

It has also recently shown that peptides of the invention can inhibit B cell function as well as T cell function (Huynh et al. 2003). IgE antibody responses are involved in both allergic asthma and non-allergic asthma. Therefore in a fourth aspect, the invention provides a method of treatment of asthma, comprising the step of administering an effective amount of a compound which has the ability to inhibit production of IgE by B cells to a subject in need of such treatment.

In different embodiments, the compound is as defined for the first and second aspects of the invention. The method may include the administration of a composition according to the third aspect of the invention.

The mammal may be a human, or may be a domestic or companion animal. While it is particularly contemplated that the compounds of the invention are suitable for use in medical treatment of humans, they are also applicable to veterinary treatment, including treatment of companion animals such as dogs and cats, and domestic animals such as horses, cattle and sheep, or zoo animals such as non-human primates, felids, canids, bovids, and ungulates.

In a third aspect, the invention provides a composition comprising a peptide or peptide-lipid conjugate as defined above, together with a pharmaceutically-acceptable carrier which is adapted to administration by inhalation.

In one embodiment the composition is in ready-to-administer form in a sealed vial, container or cartridge. Preferably the composition is sterile.

The composition may optionally comprise a stabilizer and/or a bulking agent.

In one embodiment the sealed vial, container or cartridge is an inhalation device adapted to deliver the composition to the patient via inhalation. The inhalation device may comprise an aerosol, nebuliser or dry powder delivery mechanism. Preferably the inhalation device comprises an aerosol.

Preferably the inhalation device comprises a nebuliser.

Preferably the inhalation device delivers the composition in dry powder form. Also preferably the composition does not require reconstitution before use.

In a further aspect, the invention provides an article of manufacture which comprises a composition comprising one or more peptides according to the invention in a dosage form suitable for administration by a patient.

Preferably the dosage form is labelled with, or accompanied by, instructions for treating or preventing inflammatory airway or lung disease in a human.

Preferably the dosage form is a sealed vial, container or cartridge containing a ready-to-administer pharmaceutical composition comprising one or more of peptides according to the invention.

Preferably the pharmaceutical composition is sterile.

Preferably the pharmaceutical composition comprises a stabilizer.

Preferably the pharmaceutical composition comprises a bulking agent.

Preferably the sealed vial, container or cartridge is an inhalation device adapted to deliver the pharmaceutical composition to the patient via inhalation.

Preferably the inhalation device comprises an aerosol.

Preferably the inhalation device delivers the pharmaceutical composition in dry powder form. Preferably the pharmaceutical composition does not require reconstitution before use.

In all aspects of the invention the inflammatory airway or lung disease is preferably asthma, more preferably allergic asthma.

Methods and pharmaceutical carriers for preparation of pharmaceutical compositions are well known in the art, as set out in textbooks such as Remington's Pharmaceutical Sciences, 20th Edition, Williams & Wilkins, Pennsylvania, USA.

The compounds and compositions of the invention may be administered by any suitable route, and the person skilled in the art will readily be able to determine the most suitable route and dose for the condition to be treated. Dosage will be at the discretion of the attendant physician or veterinarian, and will depend on the nature and state of the condition to be treated, the age and general state of health of the subject to be treated, the route of administration, and any previous treatment which may have been administered.

The carrier or diluent, and other excipients, will depend on the route of administration, and again the person skilled in the art will readily be able to determine the most suitable formulation for each particular case.

Methods of formulating peptides and polypeptides for delivery by inhalation are well known in the art. For example, Nektar Therapeutics (formerly Inhale Therapeutic Systems) has for many years been developing dry powder formulations and delivery devices for pulmonary delivery of proteins, peptides and other molecules through inhalation into the lung. In addition, the AERx™ pulmonary delivery device for insulin (Aradigm Corporation) is now in phase III clinical trial.

It will be clearly understood that a nucleic acid molecule encoding a peptide according to the invention, a peptidomimetic analogue of the peptide, or an ester, salt or prodrug of any of the peptide, nucleic acid or peptidomimetic is also within the scope of the invention. It will also clearly be understood that peptoids are within the scope of the invention. Peptoids are an archetypal and relatively conservative example of a peptidomimetic oligomer. Peptoids differ from peptides in the manner of side chain appendage. Specifically, the side chains of peptoid oligomers are shifted to become pendant groups of the main-chain nitrogen atoms. However, the sequence of atoms along the peptoid backbone is identical to that of the corresponding peptide.

As will be readily appreciated by those skilled in this field, hydrophobic amino acids include Ala, Val, Leu, Ile, Pro, Phe, Tyr and Met; positively-charged amino acids include Lys, Arg and His; and negatively-charged amino acids include Asp and Glu.

BRIEF DESCRIPTION OF THE FIGURES

FIG. 1 is a schematic illustration of the experimental mouse model used to test the method of the invention. This model was used to generate the data presented in FIGS. 2, 3 and 4.

FIG. 2 compares the percentages of white blood cells (eosinophils, neutrophils, lymphocytes and macrophages) in cytospin preparations of BAL fluid from treated and control mice. Group A: no treatment. Group B: 100 µl of peptide in PBS at a final concentration of 1 mM, administered i.n. 24 hours before antigen sensitization on day 1. Group C: 100 µl of peptide in PBS at a final concentration of 1 mM, administered i.n. 24 h before the i.n. challenge.

FIG. 3 shows eosinophils as a percentage of total white blood cells in lung sections from treated and control mice. Groups are: (1) no treatment (No Tx); (2) 100 µl of mock peptide in PBS at a final concentration of 50 mM administered i.n. 24 h before the i.n. challenge (mock peptide); (3) 100 µl of peptide in PBS at a final concentration of 50 mM administered i.n. 24 h before the i.n. challenge (peptide).

FIG. 4 shows the results of whole body plethysmographic measurements of the degree of airway obstruction. Groups are: (1) no treatment (No Tx); (2) 100 µl of mock peptide in PBS at a final concentration of 50 mM administered i.n. 24 h before the i.n. challenge (mock peptide); (3) 100 µl of peptide in PBS at a final concentration of 50 mM administered i.n. 24 h before the i.n. challenge (peptide).

FIG. 5 is a schematic illustration of the experimental rat model used to test the method of the invention. This model was used to generate the data in FIGS. 6-8.

FIG. 6 shows the activity of the eosinophil marker, eosinophil peroxidase, in cell-free BAL fluid from treated and vehicle control rats. The data are expressed as mean±SEM. *Significantly different from vehicle control (p<0.05). **Significantly different from vehicle control (p<0.01).

FIG. 7 shows the activity of the neutrophil marker, myeloperoxidase in cell-free BAL fluid from treated and vehicle control rats. The data are expressed as mean±SEM. *Significantly different from vehicle control (p<0.05). **Significantly different from vehicle control (p<0.01).

FIG. 8 shows the total number of inflammatory cells (leukocytes) recovered in BAL fluid from treated or vehicle control rats. The data are expressed as mean±SEM. *Significantly different from vehicle control (p<0.05). **Significantly different from vehicle control (p<0.01).

DETAILED DESCRIPTION

T cell responses are mediated by a subclass of T cells known as T helper cells. These are of two subtypes, Th-1 and Th-2. These Th-1 and Th-2 cell subtypes are believed to be derived from a common precursor, termed a Th-0 cell. In contrast to the mutually exclusive cytokine production pattern which is characteristic of the Th-1 and Th-2 subtypes, Th-0 cells produce most or all of these cytokines. The release profiles of the different cytokines for the Th-1 and Th-2 subtypes plays an active role in the selection of effector mechanisms and cytotoxic cells. The IL-2 and γ-interferon secreted by Th-1 cells tends to activate macrophages and cytotoxic cells, while the IL-4, IL-5, IL-6 and IL-10 secreted by Th-2 cells tends to increase the production of eosinophils and mast cells, as well as to enhance the production of antibodies including IgE, and to decrease the function of cytotoxic cells. Once established, the Th-1 or Th-2 response pattern is maintained by the production of cytokines which inhibit the production of the other subset. The γ-interferon produced by Th-1 cells inhibits production of Th-2 cytokines such as IL-4 and IL-10, while the IL-10 produced by Th-2 cells inhibits the production of Th-1 cytokines such as IL-2 and γ-interferon. Disturbance of the delicate balance between the cytokines produced by the Th-1 and Th-2 cell subsets leads to a host of disorders. In particular, overproduction of Th-2 cytokines leads to allergic disorders, including anaphylactic hypersensitivity, asthma, allergic rhinitis, atopic dermatitis, vernal conjunctivitis, eczema, urticaria and food allergies (Umetsu et al. 1997)

The immune response associated with the onset of asthma has mixed histopathological features, showing characteristics of both acute immune reactions and chronic, cell-mediated immune reactions. This response is characterized by the infiltration of the bronchial mucosa with neutrophils, eosinophils, macrophages, and lymphocytes (see for review Corrigan and Kay, 1992). In addition, basophils have been implicated as being a source of chemotactic factors.

A number of studies suggest that asthma is induced by antigen-specific TH2-type responses (Corrigan and Kay, 1992; Robinson et al., 1992; Romagnani et al., 1991; Kay, 1991; Walker et al., 1991).

The onset of the asthmatic response is controlled by CD4+ T-lymphocytes, which produce a characteristic Th2 pattern of lymphokine production (Kay and Corrigan, 1992), with expression of IL-4, IL-5, and IL-10 (Mosmann and Moore 1989; Mosmann et al. 1986). The individual functions of these lymphokines play a role in the asthmatic response. The expression of IgE (IL-4) (Zhang et al. 1992) and eosinophilia (IL-4/IL-5) (Spry et al. 1992) are both characteristic of asthmatic responses (Del Prete, 1992).

A primary feature of asthma is the accumulation of eosinophils in the bronchoalveolar lavage (BAL) fluid (Corrigan and Kay 1992; Arm and Lee 1992; Diaz et al. 1989). Eosinophils have also been implicated as a primary cell responsible for the induction of bronchial mucosal injury, and are thought to induce the bronchial obstruction associated with the asthmatic response (Corrigan and Kay 1992; Djukanovic et al. 1990; Walker et al. 1993). IL-4-mediated eosinophilia has been demonstrated in studies utilizing transfected tumour cells (Tepper et al. 1989) and transgenic mice (Tepper et al. 1990) suggesting that IL-4 is a primary inducer of the eosinophilic response.

This crucial role of T cell-mediated responses underlies the widespread use of immunosuppressive agents such as corticosteroids in the treatment of asthma.

The TCR is composed of at least seven transmembrane proteins. The disulfide-linked (α,β-Ti) heterodimer forms the clonotypic antigen recognition unit, while the invariant chains of CD3, consisting of ε, γ, δ, ζ and η chains, are responsible for coupling the binding of ligand to the TCR with signalling pathways which result in T-cell activation and the elaboration of the cellular immune responses. Despite the gene diversity of the TCR chains, two structural features are common to all known subunits. Firstly, they are transmembrane proteins with a single membrane-spanning domain which presumably is α-helical. Secondly, all the TCR chains have the unusual feature of possessing a charged amino acid within the predicted transmembrane domain. The invariant chains have a single negative charge, conserved between the mouse and human, and the variant chains possess one ($TCR_\beta$) or two ($TCR_\alpha$) positive charges.

Table 1 sets out the transmembrane sequences of $TCR_\alpha$ in a number of species, showing that this region is highly phylogenetically conserved, indicating that it has an important functional role. The substitutions between species are very conservative.

TABLE 1

Sequence comparison of $TCR_\alpha$ transmembrane regions (SEQ ID NOS 29-33, respectively, in order of appearance)

| SPECIES | SEQUENCE |
| --- | --- |
| MOUSE | NLSVMGLRILLLKVAGFNLLMTL |
| RAT | NLSVMGLRILLLKVAGFNLLMTL |
| SHEEP | NLSVTVFRILLLKVVGFNLLMTL |
| COW | NLSVIVFRILLLKVVGFNLLMTL |
| HUMAN | NLSVIGFRILLLKVAGFNLLMTL |

One group of peptides used in the present invention is based on a portion of the transmembrane domain of TCRα. The complete murine sequence of this portion is
  NLSVMGLRILLLKVAGFNLLMTLRLWSS (SEQ ID NO: 34), and the corresponding human sequence is
  NLSVIGFRILLLKVAGFNLLMTL (SEQ ID NO: 35).

There is complete sequence homology across a range of species in the last 15 amino acids of the $TCR_\alpha$ chain distal to the sequence upon the peptide of the present invention is based, which are shown in bold. Peptides including these additional 15 residues are expected to have activity similar to that of the peptides of the present invention. The essential feature is that the $TCR_\alpha$ transmembrane sequence-derived peptide includes two positively-charged amino acids separated by 3 to 5 hydrophobic amino acids. Furthermore, as demonstrated in PCT/AU96/00018, the peptide may be modified at the carboxy terminal without loss of activity. It is expected that modification at the amino terminal may also be made without loss of activity.

Accordingly, it is intended that the present invention includes within its scope peptides which include amino acids in addition to the "core" sequence of the TCRα transmembrane peptide of the present invention, NH2-Gly-Leu-Arg-Ile-Leu-Leu-Leu-Lys-Val-OH (SEQ ID NO: 1), and which affect the T-cell antigen receptor. Peptides whose sequence is based on, or whose sequence has functional properties equivalent to, sequences of the invariant region of (a) the TCRα transmembrane domain;
(b) the TCRβ transmembrane domain;
(c) the TCRα intracellular domain; or
(d) the CD3-γ, -δ, -ε or η chain are also within the scope of the invention, provided that they have the ability to inhibit one or more functions of the T cell receptor (TCR). Such sequences are referred to herein as being "derived from the sequence of the invariant region". It will also be clearly understood that the invention encompasses the use of nucleic acid molecules encoding peptides of the invention, peptidomimetic analogues of peptides of the invention, and esters, salts or prodrugs of any of these peptides, nucleic acid molecules, or peptidomimetic analogues.

Unless otherwise indicated, the present invention employs conventional chemistry, protein chemistry, molecular biological and enzymological techniques within the capacity of those skilled in the art. Such techniques are well known to the skilled worker, and are explained fully in the literature. See Coligan, Dunn, Ploegh, Speicher and Wingfield: "Current protocols in Protein Science" (1999) Volumes I and II (John Wiley & Sons Inc.); Sambrook, Fritsch and Maniatis: "Molecular Cloning: A Laboratory Manual" (2001); Bailey, J. E. and Ollis, D. F.: Biochemical Engineering Fundamentals, McGraw-Hill Book Company, NY, 1986; Glazer, A N, DeLange, R J, and Sigman, D S: Chemical Modification of Proteins (North Holland Publishing Company, Amsterdam, 1975); Lundblad, R L (1995) Techniques in protein modification. CRC Press, Inc. Boca Raton, Fla., USA.

It is to be clearly understood that this invention is not limited to the particular materials and methods described herein, as these may vary. It is also to be understood that the terminology used herein is for the purpose of describing particular embodiments only, and it is not intended to limit the scope of the present invention, which will be limited only by the appended claims.

The peptides of the present invention may be manufactured using recombinant technology well known to those skilled in this field. For example, the peptides may be manufactured using recombinant techniques, for example as described in Maniatis, "Recombinant DNA Methods: a Laboratory Handbook", 1985 or Molecular Cloning. A Laboratory Manual", eds Maniatis, T., Fritsch, E. F. e Sambrook, J., Cold Spring Harbor Laboratory ($2^{nd}$ edition, 1989).

Alternatively, the peptides of the present invention may be synthesized using techniques well known to those skilled in this field.

For example, the peptides may be synthesized using solution synthesis or solid phase synthesis, for example as described in Chapter 9, entitled "Peptide Synthesis", by Atherton and Sheppard in "Synthetic Vaccines" edited by Nicholson (Blackwell Scientific Publications, 1994). Preferably a solid phase support is utilised; this may be polystyrene gel beads in which the polystyrene is cross-linked with a small proportion of divinylbenzene (e.g. 1%), which is swollen by lipophilic solvents such as dichloromethane or more polar solvents such as dimethylformamide (DMF). The polystyrene may be functionalised with chloromethyl or aminomethyl groups. Alternatively, cross-linked and functionalised polydimethyl-acrylamide gel is used; this may be highly solvated and swollen by DMF and other dipolar aprotic solvents. Other supports based on polyethylene glycol, which is usually grafted or otherwise attached to the surface of inert polystyrene beads, can be utilised. In a preferred form, commercially-available solid supports or resins which are selected from PAL-PEG, PAK-PEG, KA, KR or TGR are used.

Solid state synthesis employs reversible blocking groups which have the dual function of masking unwanted reactivity in the amino, carboxy or side-chain functional groups and of destroying the dipolar character of amino acids and peptides, which render them inactive. Such functional groups include t-butyl esters of the structure $RCOOCMe_3$-CO—NHR, which are known as t-butoxy carboxyl or BOC derivatives.

The corresponding benzyl esters having the structure $RCO-OCH_2-C_6H_5$, urethanes having the structure $C_6H_5CH_2O$ CO—NFIR, which are known as the benzyloxycarbonyl or Z-derivatives, or derivatives of fluorenyl methanol and especially the fluorenyl-methoxy carbonyl (Fmoc) group may also be used. Each of these types of protecting group is capable of independent cleavage in the presence of one another, so that for example, of BOC-benzyl and Fmoc tertiary butyl protection strategies are frequently used.

A condensing agent may be used to link the amino and carboxy groups of protected amino acids or peptides by activating the carboxy group so that it reacts spontaneously with a free primary or secondary amine. Activated esters such as those derived from p-nitrophenol and pentafluorophenyl may be used for this purpose, and their reactivity may be increased by addition of catalysts such as 1-hydroxybenzotriazole. Esters of triazine DHBT (as discussed on page 215-216 of Nicholson, op. cit.) also may be used. Other acylating species are formed in situ by treatment of the carboxylic acid (i.e. the Na-protected amino acid or peptide) with a condensing reagent, and are reacted immediately with the amino component (the carboxy or C-protected amino acid or peptide). Dicyclohexylcarbodiimide, the BOP reagent (referred to on page 216 of the Nicholson reference), O'-Benzotriazole-N,N,NW-tetramethyluronium hexafluorophosphate (HBTU) and its analogous tetrafluoroborate are frequently-used condensing agents.

The first amino acid may be attached to the solid phase support in any suitable manner, for example using BOC-amino acids. In one method BOC-amino acids are attached to chloromethyl resin by warming the triethyl ammonium salts with the resin. Fmoc-amino acids may be coupled to the p-alkoxybenzyl alcohol resin in a similar manner. Alternatively various linkage agents or "handles" may be used to join the first amino acid to the resin. P-hydroxymethyl phenylactic acid linked to aminomethyl polystyrene may be used for this purpose.

It may also be possible to add various groups to the peptide of the present invention in order to confer advantages such as increased potency or extended half-life in vivo, without substantially decreasing the biological activity of the peptide. It is intended that such modifications to the peptide of the present invention which do not result in a decrease in biological activity are within the scope of the present invention.

DEFINITIONS

Asthma is a chronic disease of the airways of the lungs, characterized by inflammation and paradoxical narrowing of the bronchi. Asthma includes asthmatic conditions mediated via T-cell action, including extrinsic asthma (allergic asthma), intrinsic asthma (non-allergic asthma), mixed asthma (extrinsic and intrinsic asthma), occupational asthma induced by agents such as toluene diisocyanate, polyvinyl chloride, phthalic anhydride, trimellitic anhydride, plicatic acid (Western Red Cedar trees) or metal salts such as platinum or nickel), drug-induced asthma (including aspirin-induced asthma or asthma induced by non-steroidal anti-inflammatory drugs (NSAIDs)), exercise-induced asthma, and cough variant asthma. The symptoms, which are provoked by allergens or by environmental triggers such as tobacco smoke or other air pollutants, include wheezing, shortness of breath, difficulty in breathing, especially on exhalation, and tightness of the chest. Other triggers include infections, irritants such as strong odours from perfumes or cleaning solutions, exercise or exertion, changes in temperature or humidity, stress and strong emotion. In a preferred embodiment the asthma is an allergic or non-allergic asthmatic condition mediated by T-cell function.

Standard tests used by physicians to diagnose asthma include a detailed medical history and physical examination, spirometric breathing tests, and chest and sinus X-rays. Specific tests which may be conducted in diagnosing asthma include bronchial provocation test, exercise-induced bronchoconstriction test, and routine pulmonary function test.

Additional tests may be conducted in the management of asthma, and include allergy intradermal skin test, allergy prick skin test, CT scan of sinuses, exercise tolerance/exercise for desaturation test, pH probe test, and tailored barium swallow study. Aridol™ (Pharmaxis Ltd, French's Forest, Australia) is a dry powder inhalation test which is in clinical trial for diagnosis and monitoring of asthma.

Methods suitable for diagnosing allergic and non-allergic asthmatic conditions mediated by T-cell function, in addition to the methods described above, include measuring bronchial mucosal levels of IgE, IL-4, IL-13 and/or IL-5, and comparing the levels to a control group of patients without the asthmatic condition. Elevated bronchial levels of IgE, IL-4, IL-13 and/or IL-5 in a patient compared to those in the control group would indicate that an asthmatic condition mediated by T-cell function is present. Suitable techniques for measuring bronchial mucosal levels of IgE, IL-4 and IL-5 are well known to persons skilled in the art. Suitable techniques include bronchial lavage followed by cell population analysis, and/or bronchial biopsy followed by immunohistochemistry. Suitable reagents for immunohistochemistry include biotin-conjugated anti-human immunoglobulin E (IgE) (Cat. No. 48-139-B-0.5 mg, Antibodies Incorporated, P.O. Box 1560, Davis, Calif. 95617-1560, USA), biotin conjugated anti-human interleukin-4 (Cat. No. 13-7048, eBioscience, USA, www.ebioscience.com), and biotin conjugated anti-human interleukin-5 (Cat. No. 13-7059, eBioscience, USA, www.ebioscience.com).

Alternative methods suitable for diagnosing allergic and non-allergic asthmatic conditions mediated by T-cell function, in addition to the methods described above, include measuring the infiltration of eosinophils and Th2 cells into the bronchial mucosa, and/or measuring the presence of CC chemokines and FcεRI+ cells. The infiltration of eosinophils and Th-2 cells into the bronchial mucosa and/or the presence of CC chemokines and FEεRI+ cells, would be a characteristic of the asthmatic condition. Suitable methods used to quantify the infiltration of eosinophils and Th-2 cells into the bronchial mucosa include immunocytochemical techniques, for example those used with a fluorescence-activated cell sorter (FACS). Preferably the cells are obtained by bronchoalveolar lavage or transbronchial lung biopsy.

The measurement of eosinophil peroxidase (EPO) and myeloperoxidase (MPO) is also widely used as measure of the number of eosinohils and neutrophils respectively in BAL fluid (Strath et al. 1985; Schneider and Issekutz, 1996; Erpenbeck et al. 2003). Increased levels of EPO and MPO and other markers of eosinophil and neutrophil activation are present in the airways of asthmatic individuals even in the earliest detectable stages of the disease, and the content of EPO and MPO in plasma and the airways correlates with the level of disease activity and the response to therapy.

Methods suitable for diagnosing allergic and non-allergic asthmatic conditions mediated by B-cell function include measuring serum levels of IgE and comparing the levels to a control group of patients without the asthmatic condition. Elevated serum levels of IgE in a patient compared to those in the control group, in addition to meeting many of the criteria discussed above regarding general methods for diagnosis of an asthmatic condition, would indicate that an asthmatic condition mediated by B-cell function is present.

Asthma-related conditions include disease processes characterized by paradoxical narrowing of the bronchi, which makes breathing difficult. Symptoms of an asthma-related condition include wheezing, difficulty in breathing (particularly exhaling air) and/or tightness in the chest.

The term "chronic obstructive pulmonary disease (COPD)" refers to a group of lung diseases, including chronic bronchitis, emphysema and obliterative bronchiolitis. The most common of these diseases are chronic bronchitis and emphysema. Although a person with COPD may have either chronic bronchitis or emphysema, he or she will often have a mixture of the symptoms of these two conditions. Although emphysema usually results from damage to the lungs caused by environmental insult, usually as a result of long-term smoking, emphysema may also be caused by congenital absence of $\alpha_1$-antitrypsin in the lungs; this type of emphysema is usually inherited. A diagnostic device for early detection of COPD, "PulmoScreen™", (PulmoSonix Pty Ltd (Melbourne, Australia) is in clinical trial.

The term "T cell receptor mimic compound" means a compound which has the ability to inhibit one or more functions of the TCR, and whose structure is based on the invariant region of the $TCR_\alpha$ transmembrane domain, the $TCR_\beta$ transmembrane domain, the $TCR_\alpha$ intracellular domain, or the CD3-γ, -δ, -ε, η, or ξ chain, or is a peptide which additionally has the ability to destabilize the interchain disulphide bond between the $TCR_\alpha$ and $TCR_\beta$ chains. The compound may be a peptide, a nucleic acid molecule encoding a peptide, a peptidomimetic analogue of the peptide, or may be an ester, salt or prodrug of any of these.

The term "T cell receptor function" means a function which is mediated by T cell receptors, including but not limited to T cell activation, T cell proliferation in response to stimulation with antigen, synthesis and/or release of pro-inflammatory cytokines such as tumour necrosis factor or interleukin-1; and upregulation of cytokine receptor expression. All of these functions can be measured using assays which are well-known in the art. Thus methods for identifying inhibitors of T cell receptor function may comprise contacting a TCR polypeptide with a candidate agonist or antagonist molecule, and measuring a detectable change in one or more biological activities normally associated with the TCR polypeptide, e.g. downregulation of a Th-2 cellular function or effect.

In the claims which follow and in the description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

As used herein, the singular forms "a", "an", and "the" include the corresponding plural reference unless the context clearly dictates otherwise. Thus, for example, a reference to "an enzyme" includes a plurality of such enzymes, and a reference to "an amino acid" is a reference to one or more amino acids.

The term "alkyl" denotes a straight chain alkyl group, preferably $C_{1-30}$alkyl or cycloalkyl. Examples of straight chain alkyl groups include methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethypentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2 pentylheptyl and the like.

The term "subject" as used herein refers to any animal having a disease or condition which requires treatment with a pharmaceutically-active agent. The subject may be a human, or may be a domestic or companion animal. While it is particularly contemplated that the compounds of the invention are suitable for use in medical treatment of humans, it is also applicable to veterinary treatment, including treatment of companion animals such as dogs and cats, and domestic animals such as horses, cattle and sheep, or zoo animals such as non-human primates, felids, canids, bovids, and ungulates.

Where a range of values is expressed, it will be clearly understood that this range encompasses the upper and lower limits of the range, and all values in between these limits.

Unless defined otherwise, all technical and scientific terms used herein have the same meaning as commonly understood by one of ordinary skill in the art to which this invention belongs. Although any materials and methods similar or equivalent to those described herein can be used to practice or test the present invention, the preferred materials and methods are now described.

Abbreviations used herein are as follows:

BAL bronchoalveolar lavage

COPD chronic obstructive pulmonary disease

EPO eosinophil peroxidase i.n. intra-nasal i.p. intra-peritoneal i.t. intra-tracheal inhal. Inhalation MPO myeloperoxidase NSAID non-steroidal anti-inflammatory drug OVA ovalbumin s.c. subcutaneous Th-1 cell T helper-1 cell Th-2 cell T helper-2 cell TCR T cell receptor Peptidomimetics It is to be clearly understood that, subject to the limitations set out in the general formulae above, the invention also encompasses peptide analogues, which include but are not limited to the following:

1. Compounds in which one or more amino acids is replaced by its corresponding D-amino acid. The skilled person will be aware that retro-inverso amino acid sequences can be synthesised by standard methods; see for example Chorev and Goodman 1993;

2. Peptidomimetic compounds, in which the peptide bond is replaced by a structure more resistant to metabolic degradation. See for example Olson et al. 1993; and 3. Compounds in which individual amino acids are replaced by analogous structures for example, gem-diaminoalkyl groups or alkylmalonyl groups, with or without modified termini or alkyl, acyl or amine substitutions to modify their charge.

The use of such alternative structures can provide significantly longer half-life in the body, since they are more resistant to breakdown under physiological conditions.

Methods for combinatorial synthesis of peptide analogues and for screening of peptides and peptide analogues are well known in the art (see for example Gallop et al. 1994; Hogan, 1997).

For the purposes of this specification, the term "peptide and peptide analogue" includes compounds made up of units which have an amino and carboxy terminus separated in a 1,2, 1,3, 1,4 or larger substitution pattern. This includes the 20 naturally-occurring or "common" α-amino acids, in either the L or D configuration, the biosynthetically-available or "uncommon" amino acids not usually found in proteins, such as 4-hydroxyproline, 5-hydroxylysine, citrulline and ornithine; synthetically-derived α-amino acids, such as α-methylalanine, norleucine, norvaline, $C_\alpha$- and N-alkylated amino acids, homocysteine, and homoserine; and many others as known in the art, including β amino acids.

This term also includes compounds which have an amine and carboxyl functional group separated in a 1,3 or larger substitution pattern, such as β-alanine, γ-amino butyric acid, Freidinger lactam (Freidinger et al. 1982), the bicyclic dipeptide (BTD) (Nagai and Sato 1985), amino-methyl benzoic acid (Smythe and von Itzstein 1994), and others well known in the art. Statine-like isosteres, hydroxyethylene isosteres, reduced amide bond isosteres, thioamide isosteres, urea isosteres, carbamate isosteres, thioether isosteres, vinyl isosteres and other amide bond isosteres known to the art are also useful for the purposes of the invention.

A "common" amino acid is a L-amino acid selected from the group consisting of glycine, leucine, isoleucine, valine, alanine, phenylalanine, tyrosine, tryptophan, aspartate, asparagine, glutamate, glutamine, cysteine, methionine, arginine, lysine, proline, serine, threonine and histidine. These are referred to herein by their conventional three-letter or one-letter abbreviations.

An "uncommon" amino acid includes, but is not restricted to, one selected from the group consisting of D-amino acids, homo-amino acids, N-alkyl amino acids, dehydroamino acids, aromatic amino acids (other than phenylalanine, tyrosine and tryptophan), ortho-, meta- or para-aminobenzoic acid, ornithine, citrulline, norleucine, γ-glutamic acid, aminobutyric acid (Abu), and α,α-disubstituted amino acids.

There are believed to be two mechanisms for transporting peptides across the epithelial surface: an active mechanism, which favours ionic compounds, and a passive mechanism, which favours lipophilic compounds. It is therefore possible to adjust the bioavailability by modifying ionicity and lipophilicity. It has been observed in some cases that if the peptide also has an N-terminal amino-protecting group, this appears to improve the properties of the peptide beyond those of peptides which have a different protecting group, or none at all. In other cases the ester is cleaved under physiological conditions to release the C-terminal acid group.

Thus in order to increase bioavailability or to make the compound easier to formulate, the following changes, all of which are potentially reversible in vivo to release the "parent" compound, may be used:

(a) conversion into an acid addition salt (eg to make $NH_4^+$ $Cl^-$) or a base addition salt (to form a carboxylate ion)

(b) esterification (the ester may be cleaved in vivo by carboxyesterases)

(c) substitution at one or more amino groups. The person skilled in the art will readily be able to make these modifications, and to test which one(s) is the most suitable for the individual compound and the purpose for which it is to be used.

Pharmaceutical Agents

The methods of this invention may involve the administration of a compound of the invention, prior to, together with, or subsequent to the administration of a second pharmaceutically-active agent; or the administration of a combination of a compound of the invention and a second pharmaceutically-active agent.

As used herein, the term "therapeutically effective amount" means an amount of a compound of the present invention effective to yield a desired therapeutic response, for example to prevent or treat a disease which is susceptible to treatment by administration of a pharmaceutically-active agent comprising the compound of the invention.

The specific "therapeutically effective amount" will of course vary with such factors as the particular condition being treated, the physical condition and clinical history of the subject, the type of animal being treated, the duration of the treatment, the nature of concurrent therapy (if any), and the specific formulations employed and the structure of the compound or its derivatives. Typically, dosages used in vitro may provide useful guidance in the amounts useful for in situ administration of the pharmaceutical composition, and animal models may be used to determine effective dosages for treatment without causing undesirable side effects. For example, various considerations involved in determining the appropriate dose range are described in Langer, 1990).

As used herein, a "pharmaceutical carrier" is a pharmaceutically acceptable solvent, suspending agent, excipient or vehicle for delivering the compound of the invention and/or pharmaceutically-active agent to the subject. The carrier may be liquid or solid, and is selected with the planned manner of administration in mind.

The compound of the invention may be administered intravenously, subcutaneously, intratracheally, intrabronchially, intranasally or via inhalation in dosage unit formulations containing conventional non-toxic pharmaceutically acceptable carriers, adjuvants, and vehicles, and is preferably administered by inhalation. The invention also provides suitable aerosol or dry powder pharmaceutical formulations for use in the novel methods of treatment of the present invention.

Preservatives and other additives may also be present, such as anti-microbials, anti-oxidants, chelating agents, growth factors and inert gases and the like.

Preparations for such administration may include sterile aqueous or non-aqueous solutions, suspensions, and emulsions. Examples of non-aqueous solvents include propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media such as sodium chloride solution, Ringer's dextrose, dextrose and sodium chloride and lactated Ringer's.

Generally, the terms "treating", "treatment" and the like are used herein to mean affecting a subject, tissue or cell to obtain a desired pharmacological and/or physiological effect. The effect may be prophylactic in terms of completely or partially preventing asthma or a sign or symptom thereof, and/or may be therapeutic in terms of a partial or complete cure of asthma. "Treating" as used herein covers any treatment of, or prevention of asthma in a mammal, particularly a human, and includes preventing asthma from occurring in a subject who may be predisposed to asthma, but has not yet been diagnosed as having it; inhibiting asthma, ie arresting its development; or relieving or ameliorating the effects of asthma, ie causing regression of the effects of asthma.

The invention includes various pharmaceutical compositions useful for ameliorating asthma. The pharmaceutical compositions according to one embodiment of the invention are prepared by bringing a compound of the invention, or a prodrug, analogue, derivative or salt thereof, optionally together with one or more other pharmaceutically-active agents into a form suitable for administration to a subject, using carriers, excipients and additives or auxiliaries.

The compounds of the invention may be administered per se or in the form of a pharmaceutically acceptable salt. Such pharmaceutically-acceptable salts include, but are not limited to, those prepared from the following acids: acetic, trifluoroacetic, hydrochloric, hydrobromic, sulphuric, nitric, phosphoric, maleic, salicylic, p-toluenesulfonic, tartaric, citric, methanesulphonic, formic, malonic, succinic, naphthalene-2-sulphonic and benzenesulphonic. Pharmaceutically-acceptable salts can also be prepared as alkaline metal or alkaline earth salts, such as sodium, potassium or calcium salts of a carboxylic acid group, or as ammonium salts.

In addition, some of the compounds of the invention may form solvates with water or common organic solvents. Such solvates are encompassed within the scope of the invention.

Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 20th ed. Williams & Wilkins (2000) and The British National Formulary 43rd ed. (British Medical Association and Royal Pharmaceutical Society of Great Britain, 2002; bnf.rhn.net), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed., 1985).

The pharmaceutical compositions are preferably prepared and administered in dosage units. Different daily doses can be used for treatment of a subject, depending on the activity of the compound, the manner of administration, the nature and severity of the disorder, and the age and body weight of the subject. Under certain circumstances, however, higher or lower daily doses may be appropriate. The administration of the daily dose can be carried out by single administration in the form of an individual dosage unit or else several smaller dosage units, or by multiple administration of subdivided doses at specific intervals.

Aqueous suspensions normally contain the active materials in admixture with excipients suitable for the manufacture of aqueous suspensions. Such excipients may be suspending agents such as sodium carboxymethyl cellulose, methyl cellulose, hydroxypropylmethylcellulose, sodium alginate, polyvinylpyrrolidone, gum tragacanth and gum acacia; dispersing or wetting agents, which may be (a) a naturally occurring phosphatide such as lecithin;

(b) a condensation product of an alkylene oxide with a fatty acid, for example, polyoxyethylene stearate;

(c) a condensation product of ethylene oxide with a long chain aliphatic alcohol, for example, heptadecaethyleneoxycetanol;

(d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

Compounds of the invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Dose levels of the compound of the present invention will usually be of the order of about 0.001 mg to about 100 mg per kilogram body weight, ie. from about 0.07 mg to about 7 g per patient per day, assuming an average weight of 70 kg, with a preferred dosage range between about 0.01 mg to about 10 mg per kilogram body weight per day, i.e. from about 0.7 mg to about 700 mg per patient per day. The amount of active ingredient which may be combined with the carrier materials to produce a single dose will vary, depending upon the subject to be treated and the particular mode of administration. It will be understood, however, that the specific dose for any particular patient will depend upon a variety of factors including the activity of the specific compound employed, the age, body weight, general health, sex, diet, time of administration, route of administration, rate of excretion, drug combination and the severity of the asthma in the particular individual undergoing therapy.

In a preferred form the total concentration of the peptide fractions in any vehicle suitable for use in accordance with the present invention is sufficiently high to provide the required dose of about 0.00007-7 g/patient/day. Thus, for example, if a nebulizer administers 4 ml of solution per dose, the concentration of peptide in the solution in the case of a patient weighing 75 kg should be approximately 0.0000175-1750 mg/ml.

The invention provides for both prophylactic and therapeutic treatment of asthma with the compounds of the present invention. In the case of prophylactic treatment for allergic asthma, it is desirable to administer the said compounds to the patient up to about 24 hours prior to anticipated exposure to allergen or prior to the onset of allergic asthma. In the case of therapeutic treatment for acute asthma, including allergic asthma, it is desirable to treat the asthmatic patient as early as possible following onset of an asthma attack. In one embodiment, an episode of acute asthma is treated within 24 hours of the onset of symptoms by administration of said compounds. However, it will be appreciated that the methods of the invention can be used to ameliorate symptoms at any point in the pathogenesis of asthmatic disease. Additionally, the methods of the invention can be used to alleviate symptoms of chronic asthmatic conditions.

The compounds of the invention may additionally be combined with other compounds to provide an operative combination. It is intended to include any chemically compatible combination of pharmaceutically-active agents, as long as the combination does not eliminate the activity of the compound of the invention.

Compounds according to the invention can be formulated as discussed below to deliver a desired quantity of the active agent to the lungs of a patient by inhalation, or to the nasal respiratory epithelium as a topically applied liquid medicament.

Compositions containing the compound of the invention may be prepared in either solid or liquid form. Compositions containing respirable dry particles of micronized active agent may be prepared by grinding dry active agent with a mortar and pestle, and then passing the micronized composition through a 400 mesh screen to break up or separate out large agglomerates. Liquid compositions comprise the active agent dispersed in an aqueous carrier, such as sterile pyrogen-free saline solution or sterile pyrogen-free water. If desired, the composition may be mixed with a propellant to assist in spraying the composition and forming an aerosol thereof. The solid particulate form of the active agent may optionally contain a dispersant which serves to facilitate the formation of an aerosol. A suitable dispersant is lactose, which may be blended with the active agent in any suitable ratio (e.g., a 1 to 1 ratio by weight). The medicament compositions may be provided in unit dosage form, such as in the form of sterile ampoules or pressurized containers.

The inhalant compositions used in the present invention may comprise liquid or powdered compositions containing the peptide and suitable for nebulization and intrabronchial use, or aerosol compositions administered via an aerosol unit dispensing metered doses. Suitable liquid compositions comprise the peptide in an aqueous, pharmaceutically acceptable inhalant solvent, e.g. isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs.

Aerosol formulations for use in the method of the invention would typically include fluorinated alkane propellants, surfactants and co-solvents and may be filled into aluminium or other conventional aerosol containers, which are then closed by a suitable metering valve and pressurized with propellant. Suitable powder compositions include powdered preparations of the compound, thoroughly intermixed with lactose or other inert powders acceptable for intrabronchial administration. The powder compositions can be administered via an aerosol dispenser or encased in a breakable capsule which may be inserted by the patient into a device which punctures the capsule and blows the powder out in a steady stream suitable for inhalation.

As those skilled in the art will appreciate, many conventional methods and apparatus are available for administering precisely metered doses of intrabronchial medicaments and for regulating the desired dosage amount in accordance with patient's weight and the severity of the patient's condition. Moreover, there are many well-known liquid, powdered and aerosol vehicles suitable for the intrabronchial compositions of the present invention. The invention is not limited to any particular inert vehicles, solvents, carriers or excipients and is not restricted to any particular methods or apparatus for intrabronchial administration. See for example Corkery, K. 2000.

Liquid aerosols of respirable particles may be administered by any suitable means, such as by nebulizing a liquid composition containing the active agent (e.g., with a jet nebulizer or an ultrasonic nebulizer), and causing the patient to inhale the nebulized composition.

Any solid particulate medicament aerosol generator may be used to practice the present invention, with specific examples being given below. Aerosol generators for administering solid particulate medicaments to a human subject produce particles which are respirable, as explained above, and generate a volume of aerosol containing a predetermined metered dose of a medicament at a rate suitable for human administration. One illustrative type of aerosol generator comprises a chamber having a rotor mounted therein, which rotor carries a gelatin capsule containing a metered dose of dry particle medicament. In use the capsule is pierced, a patient inhales through the chamber, and the rotor is caused to spin at a speed sufficient to dispense the medicament to thereby form an aerosol of dry particles. A second type of illustrative aerosol generator comprises a pressurized canister containing dry particle medicament in a propellant. The propellant is discharged through a metering valve configured to dispense a metered dose of the dry particle medicament into the atmosphere. The propellant evaporates, leaving an aerosol of dry particle medicament.

Alternatively, patients maintained on a ventilating apparatus can be administered an aerosol of respirable particles by nebulizing the liquid composition and introducing the aerosol into the inspiratory gas stream of the ventilating apparatus, as described in U.S. Pat. No. 4,832,012 to Raabe and Lee.

Suitable devices for delivery of the peptide compounds of the invention via inhalation include the AeroDose Inhaler System (Aerogen (Sunnyvale, Calif.; U.S. Pat. Nos. 6,640,804, 6,629,646, 6,615,824 and 6,543,443), AIR Technology (Alkermes (Cambridge, Mass.), the AERx Pulmonary Drug Delivery System (Aradigm Corporation, Hayward, Calif.; U.S. Pat. No. 5,819,726), Spiros Pulmonary Drug Delivery System (Dura Pharmaceuticals, San Diego, Calif.; U.S. Pat. No. 6,060,069) and the Inhance Drug Delivery Platform (Inhale Therapeutic Systems, San Carlos, Calif.; U.S. Pat. Nos. 6,138,668, 5,775,320 and 5,458,135). Suitable devices for delivery of the peptide compounds of the invention via inhalation include the device disclosed in U.S. Pat. No. 6,536,427 by Glaxo Group Ltd.

Powder injection technology for delivery of DNA is also known; see for example U.S. Pat. No. 6,475,181 by PowderJect Research Limited, International Patent Applications No. PCT/US01/50673, No. PCT/US00/10766 and No. PCT/US00/30897 by Powderject Vaccines, Inc., No. PCT/GB02/02677 by Powderject Vaccines, Inc. and Powderject Research Limited, and No. PCT/GB00/00156, No. PCT/GB00/01421 and No. PCT/GB02/00114 by Powderject Research Limited.

The entire disclosures of the specifications referred to above are incorporated herein by reference.

Animal Models of Asthma

A wide variety of animal model systems for allergic asthma is known in the art. For example, various antigens have been used in asthma model systems in dogs, primates and guinea pigs (Mapp et al. 1985; Sasaki et al. 1989; Yamada et al. 1992).

Three animal models are widely used to study asthma. The first is an *Ascaris suum* parasite antigen-induced primate model system (Gundel et al. 1992; Pritchard et al. 1983).

The second model is induced in guinea pigs by various antigens (Iijima et al. 1987; Ishida et al. 1989; Vertes et al. 1987), and pharmaceuticals (Hayes et al. 1992; Obata et al. 1992). The third model is the Brown Norway (BN) rat model. The BN model mimics human allergic asthma in several respects. This rat strain exhibits a Th2-driven response to allergic sensitisation (Renzi et al. 1996) with high levels of allergen-specific IgE (Murphey, et al. 1974). Following aeroallergen challenge of sensitised animals, early- and late-phase bronchoconstrictions occur (Renzi et al. 1993), and are associated with pulmonary inflammation and bronchial hyperresponsiveness to methacholine (Elwood, 1991).

Other models include the mouse model disclosed in U.S. Pat. No. 5,911,988 by Brownell et al, and the sheep model disclosed in International patent application No. PCT/AU02/00715 by Allergenix Pty Ltd.

Models for non-allergic asthma which are suitable for testing and selecting T-cell peptides include models described in Geba et al. 1997; Houtman et al. 2003; Romijn et al.; Bloemen et al. 1996; and Kraneveld et al. 2002.

Suitable models to test the compounds of the invention in the treatment of obliterative bronchiolitis and chronic bronchitis includes the models disclosed in Alho et al. 2003; Maasilta et al. 2001; and Zhong et al. 2003.

Suitable models to test the compounds of the invention in the treatment of emphysema include the models disclosed in March et al. 2003 and Zhong et al. 2003.

The invention will now be described in detail by way of reference only to the following non-limiting examples and drawings.

Example 1

Synthesis of Peptides

The following peptide (referred to as "peptide") was used in Examples 2-5, and was synthesised to >95% purity: $NH_2$-Gly-Leu-Arg-Ile-Leu-Leu-Leu-Lys-Val-OH (SEQ ID NO: 1)

Characteristics of the peptide include: molecular weight of 1024 kD, 9 amino acids, murine TCR-α transmembrane chain of origin/domain. This peptide was synthesied by either Bachem Company, Karlsruhe, FRG or UCB BioProducts, Belgium.

The following negative control peptide, referred to as "mock peptide", was used in Examples 2 and 3, and was also synthesised to >95% purity: $NH_2$-Leu-Gly-Ile-Leu-Leu-Leu-Gly-Val-OH (SEQ ID NO: 36). The mock peptide was synthesised by Bachem Company, Karlsruhe, FRG.

Example 2

Effect of TCR Mimic Peptides in a Murine Model of Asthma

A murine model in which immunization with ovalbumin (OVA) is used to induce asthma-like symptoms in normal Balb/c mice was employed. This model is described in Archer et al. 2004.

This model does not require the use of transgenic mice, and experiments can be performed with a variety of different standard mouse strains. The model is illustrated in FIG. 1.

Mice were immunized against OVA by i.p. injection and fourteen days later an intra-nasal (i.n.) challenge dose of OVA protein was administered. Three days later the degree of airway inflammation was assessed by bronchoalveolar lavage (BAL,) followed by counting the infiltrating leukocytes. In addition, the lungs were sectioned and stained with haematoxylin and eosin for histological analysis. In a preliminary experiment, live mice were monitored after treatment using whole body plethysmography to assess the degree of airway obstruction.

Immunization Against OVA

Female BALB/c mice (6-8 wk of age) were injected i.p. with 10 μg of OVA (Sigma-Aldrich, St. Louis, Mo.) in 200 μl of alum adjuvant (Serva, Heidelberg, Germany) on day 1. Fourteen days after the i.p. immunization, mice were anaesthetized by an i.p. injection of a mixture of ketamine and xylazine (Sigma-Aldrich), and treated i.n. with 50 μl of PBS containing 100 μg of OVA.

TCR Peptide Administration

In preliminary experiments the peptide or "mock" peptide was given at either of two different time points (24 h prior to i.p. OVA sensitization or 24 h prior to i.n. OVA challenge) at a final concentration of either 1 mM (solution) or 50 mM (suspension) in phosphate-buffered saline (PBS; 0.02 M sodium phosphate buffer with 0.15 M sodium chloride, pH adjusted to 7.4.). The 50 mM concentration of the TCR peptide was chosen because 500 μM was the optimal blocking concentration for T cells in in vitro experiments. However, experiments using titration of the peptide will be used to determine the optimal dose. A 100 μl volume of formulated peptide was administered to the mice intranasally.

The experimental groups were as follows:
  A.: No treatment
  B.: 100 μl of peptide or "mock" peptide formulated (suspended) in PBS at a final concentration of 1 or 50 mM, administered i.n. immediately before the initial immunization at day 1
  C.: 100 μl of peptide or "mock" peptide formulated (suspended) in PBS at a final concentration of 1 or 50 mM, administered i.n. 24 h immediately before the i.n. challenge.

Bronchoalveolar Lavage (BAL)

Three days after the i.n. challenge with OVA, the mice from the different groups were sacrificed, the tracheas were cannulated, and a BAL was performed by flushing lung and airways five times with 1 ml of PBS. BAL cells were counted and spun on to glass slides using a cytospin (Shandon Southern Products, Asmoor, U.K.), and then stained with Diff-Quik (Roche Diagnostics, Mannheim, Germany) according to the manufacturer's instructions. In instances where the cell number was less than $5\times10^4/200$ μl, the volume was made up to 200 μl regardless of final concentration.

Percentages of macrophages, lymphocytes, neutrophils, and eosinophils were determined microscopically using standard histological criteria. The results are summarized in FIG. 2.

Lung Histology

On days 1-6 after the last intranasal challenge with either OVA or saline, the lungs were analyzed by histology. One lobe of each lung was fixed in 10% formalin, dehydrated, mounted in paraffin, sectioned, and stained with hematoxylin and eosin according to conventional methods. The number of eosinophils in the lungs was quantified microscopically using a calibrated stage. The results are shown in FIG. 3, in which counts are given as % eosinophils per square millimeter.

Cytokine Production

Ex vivo cytokine production by T cells from lung tissue and lung lymph nodes may be assessed using antibodies against specific cytokines, such as IL-4, IL-5, IL-6 and IL-10. Such antibodies are commercially available.

T cells are prepared from lung tissue or lung lymph nodes, and are analysed by intracellular staining using FACS. Alternatively T cell culture supernatants are assayed by ELISA in order to determine the cytokine profile, using conventional methods.

Example 3

Measurement of Airway Hyperreactivity

The effects of antigen challenge on airway hyperreactivity of mice in the experimental model described above can be measured by whole body plethysmography. This can be used to make an accurate comparison with the airway hyperreactivity observed in human asthmatics. The mice are anesthetized with pentobarbitol (70-90 mg/kg body weight, i.p.), and the jugular vein is cannulated with PE 10 silastic tubing. The tracheae are then intubated with a specially-angled 18 gauge needle, the chest opened, and the tubing connected to a Harvard ventilator (tidal volume=0.2 ml, frequency 120 breaths/min, positive end-expiratory pressure 2.5-3.0 cm $H_2O$) and placed in a whole body plethysmograph. This ventilation maintains normal arterial blood gases in the subject mouse. The dead space volume is 0.025 ml.

Whole body plethysmography was used in a kinetic study from days 0-6 after treatment of mice using the model described above. The results are shown in FIG. 4.

The results of two independent experiments with pooled data show that in group C (peptide) there was a significant decrease in eosinophilia in both BAL and on lung histology. The results in a preliminary experiment with whole body plethysmography showed significant effects in treated animals.

The data demonstrate that treatment of asthmatic mice with a TCR mimic peptide reduces asthma symptoms in a non-transgenic system.

Example 4

Effect of TCR Mimic Peptides in a Rat Model of Asthma

The Brown Norway rat model was also employed to test the effects of TCR mimic peptides on reducing the symptoms of asthma. Similarly to the murine model described above, this model also involves immunisation with OVA. The model is described in Elwood, 1991. The model is illustrated in FIG. 5. In this model 10 rats were used per treatment group.

Rats were immunized against OVA by s.c. injection on Day 1, 14 and 21, and on Day 28 an inhalation challenge dose of OVA protein was administered. One day later (Day 29) the degree of airway inflammation was assessed by bronchoalveolar lavage (BAL), followed by counting of the infiltrating leukocytes and measurement of the activity of eosinophil peroxidase and myeloperoxidase.

Immunization Against OVA

Male Brown Norway rats (approximately 8 wks of age) were injected s.c. with 10 µg of OVA in 1 ml of alum adjuvant on day 1, 14 and 21. Concurrently, the animals received an i.p. injection of 0.25 ml *Bordetella pertussis* vaccine (Trivax-Evans Medical). Seven days. after the final sensitizing dose, the animals were restrained and exposed, nose only, to an aerosol of 10 mg/ml OVA for 1 h using a Wright nebuliser.

TCR Peptide Administration

In these experiments the peptide was administered either intra-tracheally (i.t) (3 mg/ml, 50 µl in 0.9% saline per rat, 24 hours before OVA challenge), intra-nasally (i.n.) (50 mg/ml, 100 µl in 0.9% saline per rat, 24 hours before OVA challenge) or by inhalation (0.1 mg/ml in 0.9% saline, 50 ml delivered by aerosol at a flow rate of 1 ml/min, for a total of 50 minutes, using a Wright nebuliser to ten (10) rats, 24 h and 4 h prior to OVA challenge). Budesonide (5 mg/ml in 90% saline/10% ethanol) was used as a positive control and was delivered by inhalation 24 h and 4 h prior to OVA challenge.

Bronchoalveolar Lavage (BAL)

Twenty-four hours after the challenge with OVA, the rats from the different groups were anaesthetized by an i.p injection of sodium pentobarbital (100 mg/kg). Following tracheal cannulation a BAL was performed by flushing lung and airways twice with 4 ml of Hank's balanced salt solution. The BAL fluid was centrifuged and the collected cells resuspended in 2 ml of PBS and the total number of leukocytes recovered were counted. The activity of eosinophil peroxidase and myeloperoxidase in the supernatant, following centrifugation (i.e., the cell-free BAL fluid) was determined by the method described in Schneider et al. 1997. The results are summarized in FIGS. 6, 7 and 8.

Example 5

Testing of Further Peptides

Additional peptides which are tested by the methods described in Examples 2, 3 and 4 are summarised in Table 2, in which the conventional single-letter code for amino acids is used.

TABLE 2

Additional TCR-derived peptides to be tested
(SEQ ID NOS 3, 11, 14, 36, 2, 12, 37, 10,
15, 38, 39, 25, 20, 19, 21, 40 and 18,
respecitively, in order or appearance)

| Peptide | Sequence | Mol Wt | No. of AAs | Chain of Origin/Domain |
|---|---|---|---|---|
| CP (human) | G F R I L L L K V | 1058 | 9 | TCR-α transmembrane |
| A | M G L R I L L L | 928 | 8 | TCR-α transmembrane |
| B | I L L L K V A G | 826 | 8 | TCR-α transmembrane |
| C | L G I L L L G V | 797 | 8 | TCR-α transmembrane |
| D | L K I L L L R V | 967 | 8 | TCR-α transmembrane |
| E | L D I L L L E V | 927 | 8 | TCR-α transmembrane |
| F | L R I L L L I K V | 1080 | 9 | TCR-α transmembrane |
| G | L R L L L K V | 854 | 7 | TCR-α transmembrane |
| H | L R I L L L G V | 896 | 8 | TCR-α transmembrane |
| I | G I L L L K V | 868 | 7 | TCR-α transmembrane |
| J | Y G R A D G G I T S | 1042 | 10 | TCR-α extracellular |
| K | S S D V P C D A T L T | 1108 | 11 | TCR-β extracellular |
| L | I V I V D I C I T | 988 | 9 | CD3-ε transmembrane |
| M | I I V T D V I A T L | 1057 | 10 | CD3-δ transmembrane |
| N | F L F A E I V S I | 1038 | 9 | CD3-γ transmembrane |
| O | A G F N L L M T | 866 | 8 | TCR-α intracellular |
| P | L L M T L R L W S S | 1220 | 10 | TCR-β intracellular |

Example 6

Further In Vitro Testing of Candidate Peptides

Additional in vitro methods of testing candidate peptides and selecting peptides suitable for use in accordance with the invention include the methods described in PCT/AU96/00018 and in Manolios et al. 1997.

An antigen presentation assay is used to evaluate the ability of the T-cell mimic peptides to inhibit T-cell activation following antigen recognition, by measuring levels of Interleukin-2 (IL-2), a product of T-cell activation.

The following cell lines are used:

(i) 2B4.11, a T-cell hybridoma which expresses a complete antigen receptor on the cell surface and produces IL-2 following recognition of the antigen cytochrome c (Samelson et al. 1983);

(ii) an interleukin-2 dependent T-cell line (CTLL) for conventional biological IL-2 assays; and (iii) the B-cell hybridoma cell line LK 35.2 (LK, I-$E^k$ bearing; (Kappler et al. 1982), which acts as the antigen-presenting cell.

It will be appreciated that other hybridoma cell lines specific for different antigens may alternatively be used. The hybridomas are grown in RPMI 1640 medium containing 10% foetal calf serum, gentamycin (80 μg/ml) and 0.002% mercaptoethanol.

The final concentration of peptide or lipopeptide in the assay generally ranges from 5 μM to 250 μM, but may be higher or lower, depending on the individual compound. In general it is expected that lower concentrations of lipopeptides are required in comparison to peptides. Preincubation of peptide in medium at 37° C. prior to addition to the assay may improve solubility and activity.

For the assay, cells are cultured together with antigen for 16 hr in microtitre wells. Each well contains $2 \times 10^4$ 2B4.11 T-cell hybridoma cells, $2 \times 10^4$ LK35.2 antigen-presenting cells and 50 μM pigeon cytochrome c (Sigma, USA; dissolved in PBS). The assay is performed in triplicate. Supernatants are recovered and the IL-2 content is determined by CTLL proliferation. The incorporation of $^3$H-thymidine is directly proportional to the amount of IL-2 present in the supernatant. The ability of different peptides to inhibit IL-2 production is examined. In addition to measuring $^3$H-thymidine incorporation, the concentration of IL-2 (IU/ml) is also determined. Control peptides include other peptides, which may be derived from a variety of sources, which have lengths equivalent to those of the candidate peptides. In additional control samples either cytochrome c (antigen) or LK cells (antigen presenting cells) is omitted.

The preferred peptides and lipopeptides of the invention have previously been found to have activity in this assay (PCT/AU96/00618; PCT/AU97/00367; Manolios et al. 1997).

Example 7

Dose-Response Relationship

The effective dose range for each of the types of compound according to the invention is determined using the model described in Example 1. A suitable test range of doses will depend on the potency of the peptide in vitro, and for example may be selected on the basis of results in the antigen presentation assay described in Example 6. For example, for peptide or palmitic acid-peptide a concentration range of 0.1 to 100 mM may be used, suitably in a volume of 100 μl. For cDNA, approximately 1 to 100 μg of plasma DNA encoding the peptide may be used. The person skilled in the art will readily be able to determine a suitable dose range for each compound to be tested. See for example Enk and Knop 2000 and Gollner et al. 2000; Hengge et al. 1995, and Hengge et al. 1998.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Alho H. S., Maasilta P. K., Harjula A. L. J., Hammainen P, Salminen J., Salminen U., 2003. Tumor necrosis factor-alpha in a porcine bronchial model of obliterative bronchiolitis. Transplantation. 76:516-23

Archer A. J., Cramton J. L., Pfau J. C., Colasurdo G., Holian A. 2004. Airway responsiveness after acute exposure to urban particulate matter 1648 in a DO11.10 murine model. Am. J. Physiol. Lung Cell Mol. Physiol. 286:L337-43

Arm J. P. and Lee T. H. 1992. The pathobiology of bronchial asthma. Adv. Immunol. 51:323-382

Bloemen P G, Buckley T L, van den Tweel M C, Henricks P A, Redegeld F A, Koster A S and Nijkamp F P. 1996. LFA-1, and not Mac-1, is crucial for the development of hyper-reactivity in a murine model of nonallergic asthma. Am. J. Respir. Crit. Care Med. 153:521-529

Chorev, M. and Goodman, M. 1993. A dozen years of retro-inverso peptidomimetics. Acc. Chem. Res., 26 266-273

Corkery, K. Inhalable Drugs for Systemic Delivery, Respiratory Care July 2000

Corrigan C. J. and Kay A. B. 1992. Asthma, eosinophils and neutrophils. Br. Med. Bull. 48:51-64

Corrigan C. J. and Kay A. B. 1992. T cells and eosinophils in the pathogenesis of asthma. Immunol Today 13:501-507

Corrigan C. J. and Kay A. B. 1992. Asthma. Role of T-lymphocytes and lymphokines. Br. Med. Bull. 48:72-84

Del Prete G. 1992. Human Th1 and Th2 lymphocytes: their role in the pathophysiology of atopy. Allergy 47:450-455

Diaz P., Gonzalez M. C., Galleguillos F. R., Ancic P., Cromwell O., Shepherd D., Durham S. R., Gleich G. J., Kay A. B. 1989. Leukocytes and mediators in bronchoalveolar lavage during allergen-induced late-phase asthmatic reactions. Am. Rev. Respir. Dis. 139:1383-1389

Djukanovic R., Roche W. R., Wilson J. W., Beasley C. R. W., Twentyman O. P., Howarth P. H., Holgate S. T. 1990. Mucosal inflammation in asthma. Am. J. Respir. Dis. 142:434-457

Elwood W. 1991. Characterisation of allergen-induced bronchial hyperresponsivness and airway inflammation in actively sensitised brown Norway rats. J. Allergy Clin. Immunol. 88:951-960

Enk A. and Knop J. 2000 T cell receptor mimic peptides and their potential application in T-cell-mediated disease. Int. Arch. Allergy Immunol. 123:275-281

Erpenbeck V. J., Hohlfeld J. M., Petschallies J., Eklund E., Peterson C. G., Fabel H., Krug N. 2003. Local release of eosinophil peroxidase following segmental allergen provocation in asthma. Clin. Exp. Allergy. 33:331-336

Freidinger R. M., Perlow D. S., Veber D. F. 1982. Protected lactam-bridged dipeptides for use as conformational constraints in peptides. J. Org. Chem. 47: 104-109

Gallop, M. A., Barrett R. W., Dower W. J., Fodor S. P., Gordon E. M. 1994. Applications of combinatorial technologies to drug discovery. 1. Background and peptide combinatorial libraries. J. Med. Chem. 37:1233-1251

Geba G. P., Wegner C. D., Wolyniec W. W., Li Y., Askenase P. W. 1997. Non-atopic asthma: in vivo airway hyperreactivity adoptively transferred to naive mice by THY-1(+) and B220(+) antigen-specific cells that lack surface expression of CD3. J. Clin. Invest. 100:629-638

Gollner G. P., Alt R., Knop J., Enk A. H. 2000 Therapeutic application of T cell mimic peptides or cDNA in the treatment of T cell-mediated skin diseases. Gene Therapy. 7:1000-1004

Gundel R. H., Wegner C. D., Letts L. G. 1992. Antigen-induced acute and late-phase responses in primates. Am. Rev. Respir. Dis. 146:369-373

Hayes J. P., Lötvall J. O. Baraniuk J., Daniel R. Barnes P. J., Taylor A. J., Chung K. F. 1992. Bronchoconstriction and airway microvascular leakage in guinea pigs sensitized with trimellitic anhydride. Am. Rev. Respir. Dis. 146: 1306-1310

Hengge U. R., Chan E. F., Foster R. A., Walker P. S., and Vogel J. C. 1995. Cytokine gene expression in epidermis with biological effects following injection of naked DNA. Nat. Genet. 10:161-6

Hengge U. R., Pfutzner W., Williams M., Goos M., Vogel J. C. 1998. Efficient expression of naked plasmid DNA in mucosal epithelium: prospective for the treatment of skin lesions. J. Invest. Dermatol. 111:605-608

Hogan J. C. 1997. Combinatorial chemistry in drug discovery. Nature Biotechnology. 15:328-330

Houtman R., Krijsveld J., Kool M., Romijn E. P., Redegeld F. A., Nijkamp F. P, Heck A. J. R., Humphery-Smith I. 2003. Lung proteome alterations in a mouse model for nonallergic asthma. Proteomics. 3:2008-18

Humbert M., Menz G., Ying S., Corrigan C. J., Robinson D. S., Durham S. D., and Kay A. B. 1999 The immunology of extrinsic (atopic) and intrinsic (non-atopic) asthma: more similarities than differences. Immunology Today, 20:528-533

Huynh N. T., Ffrench R. A., Boadle R. A., Manolios N. 2003. Transmembrane T-cell receptor peptides inhibit B- and natural killer-cell function. Immunology. 108:458-64

Iijima H., Ishii M., Yamauchi K., Chao C. L., Kimura K., Shimura S., Shindoh Y., Inoue H., Mue S., Takishima T. 1987. Bronchoalveolar lavage and histologic characterization of late asthmatic response in guinea pigs. Am. Rev. Respir. Dis. 136:922-929

Ishida K., Kelly L. J., Thomson R. J., Beattie L. L., Schellenberg R. R. 1989. Repeated antigen challenge induces airway hyperresponsiveness with tissue eosinophilia in guinea pigs. J. Appl. Physiol. 67:1133-1139

Kappler J., White J., Wegmann D., Mustain E., Marrack P. 1982. Antigen presentation by Ia+ B cell hybridomas to H-2-restricted T cell hybridomas. Proc. Natl. Acad. Sci. USA 79:3604-3607

Kay A. B. 1991. T lymphocytes and their products in atopic allergy and asthma. Int. Arch. Allergy Appl. Immunol. 94:189-193

Kay A. B. and Corrigan C. J. 1992. Asthma, eosinophils and neutrophils. Br. Med. Bull. 48:51-64

Kraneveld A. D., van der Kleij H. P. M., Kool M., van Houwelingen A. H., Weitenberg A. C. D., Redegeld F. A. M. and Nijkamp F. P. 2002. Key role for mast cells in non-atopic asthma. J. Immunol. 169:2044-2053

Langer R. 1990. New methods of drug delivery. Science, 249:1527-33

Maasilta P. K., Salminen U, Lautenschlager I. T., Taskinen E. I., Harjula A. L. J. 2001. Immune cells and immunosuppression in a porcine bronchial model of obliterative bronchiolitis. Transplantation. 72:998-1005

Manolios N., Collier S., Taylor J., Pollard J., Harrison L. C., Bender V. 1997. T-cell antigen receptor transmembrane peptides modulate T-cell function and T-cell mediated disease. Nature Medicine. 3:84-88

Manolios N., Huynh N. T., Collier S. 2002. Peptides in the treatment of inflammatory skin disease. Australasian J. Dermatol. 45:226-228

Mapp C., Hartiala J., Frick O. L., Shields R. L., Gold W. M. 1985. Airway responsiveness to inhaled antigen, histamine, and methacholine in inbred, ragweed sensitive dogs. Am. Rev. Respir. Dis. 132:292-298

March T. H., Green F. H., Hahn F. F., Nikula K. J. 2000. Animal models of emphysema and their relevance to studies of particle-induced disease. Inhal. Toxicol. 4:155-87

Metzger J. W., Beck-Sickinger A. G., Loleit M., Eckert M., Bessler W. G., Jung G. 1995. Synthetic S-(2,3-dihydroxypropyl)-cysteinyl peptides derived from the N-terminus of the cytochrome subunit of the photoreaction centre of *Rhodopseudomonas viridis* enhance murine splenocyte proliferation. J. Pept. Sci. 1:184-90

Mosmann T. R. and Moore, K. W. 1989. The role of IL-10 in cross-regulation of Th1 and Th2 response. Immunol. Today 12:A49-A58

Mosmann T. R., Cherwinski H., Bond M. W., Giedlin M. A., Coffman R. L. Mosmann T. R. et al. 1986. Two types of murine helper T cell clone. J. Immunol. 136:2348-2359

Murphey S. M., Brown S., Miklos N., Fireman P. 1974. Reagin synthesis in inbred strains of rats. Immunology 27:245-253

Nagai U. and Sato K. 1985. Synthesis of a bicyclic dipeptide with the shape of β-turn central part. Tetrahedron Lett. 26:647-650

Obata H., Tao Y., Kido M., Nagata N., Tanaka I., Kuroiwa A. 1992. Guinea pig model of immunologic asthma induced by inhalation of trimellitic anhydride. Am. Rev. Respir. Dis. 146:1553-1558

Olson G. L., Bolin D. R., Bonner M. P., Bos M., Cook C. M., Fry D. C., Graves B. J., Hatada M., Hill D. E., Kahn M. 1993. Concepts and progress in the development of peptide mimetics J. Medicinal Chem., 36:3039-3049

Pritchard D. I., Eady R. P., Harper S. T., Jackson D. M., Orr T. S., Richards I. M., Trigg S., Wells E. 1983. Laboratory infection of primates with *Ascaris suum* to provide a model of allergic bronchoconstriction. Clin. Exp. Immunol. 54:469-476

Renzi P. M., Olivenstein R., Martin J. G. 1993. Inflammatory cell populations in the airways and parenchyma after antigen challenge in the rat. Am. Rev. Respir. Dis. 147:967-974

Renzi P. M., al Assaad A. S., Yang J., Yasruel Z., Hamid Q. 1996. Cytokine expression in the presence or absence of late airway responses after antigen challenge of sensitised rats. Am. J. Respir. Cell Mol. Biol. 15:367-373

Robinson D. S., Hamid Q., Ying S., Tsicopoulos A., Barkans J., Bentley A. M., Corrigan C., Durham S. R., Kay A. B. 1992. Predominant Th2-like bronchoalveolar T-lymphocyte population in atopic asthma. N Engl. J. Med. 326:298-304

Romagnani S., Maggi E., Parronchi P., Macchia D., Piccinni M. P., Ricci M. 1991. Increased numbers of TH2-like CD4+ T cells in target organs and in the allergen-specific repertoire of allergic patients. Int. Arch. Allergy Appl. Immunol. 94:133-136

Romijn E., Krijsveld J., van der Staaij A., Houtman R., Redegeld F., Heck A. J. R., Humphery-Smith I. Identification of novel target molecules in asthma using two-dimensional gel electrophoresis and mass-spectrometry: Poster Presentation, 4th SIENA Meeting, From Genome to Proteome: Knowledge Acquisition and Representation, Sep. 4-7, 2000, Siena, Italy, Auditorium Istituti Biologici, Via Laterina 8, Siena Samelson L. E., Germain R. N., Schwartz R. H. 1983. Monoclonal antibodies against the antigen receptor on a cloned T-cell hybrid. Proc. Natl. Acad. Sci. USA. 80:6972-6

Sasaki H., Yanai M., Shimura S., Okayama H., Aikawa T., Sasaki T., Takishima T. 1989. Late asthmatic response to *Ascaris* antigen challenge in dogs treated with metyrapone. Am. Rev. Respir. Dis. 136:1459-1465

Schneider T. and Issekutz A. C. 1996. Quantitation of eosinophil and neutrophil infiltration into rat lung by specific assays for eosinophil peroxidase and myeloperoxidase. Application in a Brown Norway rat model of allergic pulmonary inflammation. J. Immunol. Methods. 198:1-14

Schneider T., van Velzen D., Moqbel R., Issekutz A. C. 1997. Kinetics and Quantitation of eosinophil and neutrophil recruitment to allergic lung inflammation in a Brown Norway Rat model. Am. J. Respir. Cell Mol. Biol. 17:702-712

Smythe M. L. and von Itzstein M. 1994. Design and synthesis of a biologically active antibody mimic based on an antibody-antigen crystal structure. J. Am. Chem. Soc. 116: 2725-2733

Spry C. J., Kay A. B., Gleich G. J. 1992. Eosinophils. Immunol. Today 13:384-387

Strath M., Warren D. J., Sanderson C. J. 1985. Detection of eosinophils using an eosinophil peroxidase assay: its use as an assay for eosinophil differentiation factors. J. Immunol. Methods 83:209-215

Svartengren K., Ericsson C. H., Svartengren M., Mossberg B., Philipson K., Camner P. 1996 Deposition and clearance in large and small airways in chronic bronchitis. Exp. Lung Res. 22:555-76

Tepper R. I., Pattengale P. K., Leder P. 1989. Murine interleukin-4 displays potent anti-tumor activity in vivo. Cell 57:503-512

Tepper R. I., Levinson D. A., Stanger B. Z., Campos-Torres J., Abbas A. K., Leder P. 1990. IL-4 induces allergic-like inflammatory disease and alters T cell development in transgenic mice. Cell 62:457-467

Umetsu D. T., DeKruyff R. H. 1997. Th1 and Th2 CD4+ cells in the pathogenesis of allergic diseases. Proc. Soc. Exp. Biol. Med. 215:11-20

Vertes C., Gonczy S., Lendvay N., Debreczeni L. A. 1987. A model for experimental asthma: provocation in guineapigs immunized with *Bordetella perussis*. Bull. Eur. Physiopathol. Respir. 10:111s-113s Walker C., Virchow J. C. Bruijnzeel P. L. B., Blaser K. 1991. T cells and asthma II: Regulation of the eosinophilia of asthma by T cell cytokines. Int. Arch. Allergy Appl. Immunol. 94:248-250

Walker C., Rihs S., Braun R. K., Betz S., Bruijnzeel P. L. 1993. Increased expression of CD11b and functional changes in eosinophils after migration across endothelial cell monolayers. J. Immunol. 150:4061-4071

Wang X. M., Djordjevic J. T., Kurosaka N., Schibeci S., Lee L., Williamson P., Manolios N. 2002 T-cell antigen receptor peptides inhibit signal transduction within the membrane bilayer. Clin Immunol. 105:199-207

Whittaker R. G., Hayes P. J., Bender V. 1993. A gentle method for linking TRIS to amino acids and peptides. Peptide Research. 6:125-128

Wiesmuller K. H., Bessler W., Jung G. 1983. Synthesis of the mitogenic S-[2,3-bis(palmitoyloxy)propyl]-N-palmitoylpentapeptide from *Escherichia coli* lipoprotein Z. Physiol. Chem. 364:593-606

Yamada N., Kadowaki S., Umezu K. 1992. Development of an animal model of late asthmatic response in guinea pigs and effects of anti-asthmatic drugs. Prostaglandins 43:507-521

Zhang X., Polla B., Hauser C., Zubler R. H. 1992. T cells from atopic individuals produce IgE-inducing activity incompletely blocked by anti-interleukin-4 antibody. Eur. J. Immunol. 22:829-833

Zhong X. N., Bai J., Shi H. Z., Wu C., Liang G. R., Feng Z. B. 2003. An experimental study on airway inflammation and remodeling in a rat model of chronic bronchitis and emphysema Zhonghua Jie He He Hu Xi Za Zhi. 26:750-755

The invention claimed is:

1. A method of treatment of inflammatory airway or lung disease, comprising the step of administering an effective amount of a peptide which has the ability to inhibit one or more functions of the T cell receptor (TCR) to a subject in need of such treatment, in which the peptide has a sequence selected from the grow consisting of:

$NH_2$-Gly-Leu-Arg-Ile-Leu-Leu-Leu-Lys-Val-OH; (SEQ. ID. NO. 1)

$NH_2$-Leu-Lys-Ile-Leu-Leu-Leu-Arg-Val-OH; (SEQ. ID. NO. 2)

$NH_2$-Gly-Phe-Arg-Ile-Leu-Leu-Leu-Lys-Val-OH; (SEQ. ID. NO. 3)

$NH_2$-Val-Phe-Arg-Ile-Leu-Leu-Leu-Lys-Val-OH; (SEQ. ID. NO. 4)

$NH_2$-Phe-Lys-Ile-Leu-Leu-Leu-Arg-Val-OH; (SEQ. ID. NO. 5)

$NH_2$-Ala-Arg-Leu-Pro-Val-Leu-Lys-Leu-Val-OH; (SEQ. ID. NO. 6)

$NH_2$-Arg-Val-Met-Ala-Pro-Arg-Ala-Leu-Leu-OH; (SEQ. ID. NO. 7)

$NH_2$-Val-Lys-Leu-Phe-Pro-Val-Lys-Leu-Phe-Pro-OH; (SEQ. ID. NO. 8)

$NH_2$-Leu-Arg-Ile-Leu-Leu-Leu-Ile-Lys-Val-OH; (SEQ. ID. NO. 9)

```
                                                    (SEQ. ID. NO. 10)
NH2-Leu-Arg-Leu-Leu-Leu-Lys-Val-OH.

(SEQ. ID. NO. 11)
NH2-Met-Gly-Leu-Arg-Ile-Leu-Leu-Leu-OH;

(SEQ. ID. NO. 12)
NH2-Leu-Asp-Ile-Leu-Leu-Leu-Glu-Val-OH;

(SEQ. ID. NO. 13)
NH2-Ile-Leu-Leu-Leu-Lys-Val-Ala-Gly-Phe-OH;

(SEQ. ID. NO. 14)
NH2-Ile-Leu-Leu-Leu-Lys-Val-Ala-Gly-OH;

(SEQ. ID. NO. 15)
NH2-Leu-Arg-Ile-Leu-Leu-Leu-Gly-Val-OH;

(SEQ. ID. NO. 16)
NH2-Leu-Gly-Ile-Leu-Leu-Leu-Lys-Val-OH;

(SEQ. ID. NO. 17)
NH2-Ile-Leu-Leu-Gly-Lys-Ala-Thr-Leu-Tyr-OH;

(SEQ. ID. NO. 18)
NH2-Leu-Leu-Met-Thr-Leu-Arg-Leu-Trp-Ser-Ser-OH;

(SEQ. ID. NO. 19)
NH2-Ile-Ile-Val-Thr-Asp-Val-Ile-Ala-Thr-Leu-OH;

(SEQ. ID. NO. 20)
NH2-Ile-Val-Ile-Val-Asp-Ile-Cys-Ile-Thr-OH;

(SEQ. ID. NO. 21)
NH2-Phe-Leu-Phe-Ala-Glu-Ile-Val-Ser-Ile-OH;

(SEQ. ID. NO. 22)
NH2-Tyr-Gly-Arg-Ala-Asp-Cys-Gly-Ile-Thr-Ser-OH;

(SEQ. ID. NO. 23)
NH2-Trp-Gly-Arg-Ala-Asp-Cys-Gly-Ile-Thr-Ser-OH;

(SEQ. ID. NO. 24)
NH2-Tyr-Gly-Arg-Ala-Asp-Cys-Ile-Thr-Ser-OH;
and (SEQ. ID. NO. 25)
NH2-Ser-Ser-Asp-Val-Pro-Cys-Asp-Ala-Thr-Leu-Thr-
OH;
``` wherein the C-terminus of said peptide is conjugated to a lipid moiety selected from: N-palmitoyl-S-[2,3-bis(palmitoyloxy) propyl]cysteine (Pam3Cys), or an analogue thereof in which only two acyl substituents are present.

2. A method according to claim 1, in which the peptide is NH2-Leu-Arg-Ile-Leu-Leu-Leu-Gly-Val-OH (SEQ. ID. NO. 15), NH2-Leu-Leu-Met-Thr-Leu-Arg-Leu-Trp-Ser-Ser-OH (SEQ. ID. NO. 18) or NH2-Ile-Val-Ile-Val-Asp-Ile-Cys-Ile-Thr-OH (SEQ. ID. NO. 20).

3. A method according to claim 1, in which the peptide is NH2-Ile-Val-Ile-Val-Asp-Ile-Cys-Ile-Thr-OH (SEQ. ID. NO. 20).

4. A method according to claim 1, in which the peptide comprises a cysteine residue, and has the ability to destabilize the interchain disulphide bond between the $TCR_\alpha$ and $TCR_\beta$ chains.

5. A method of treatment of inflammatory airway or lung disease, comprising the step of administering an effective amount of a peptide which has the ability to inhibit one or more functions of the T cell receptor (TCR) to a subject, in which the peptide has a sequence selected from the group consisting of:

```
                                                    (SEQ. ID. NO. 1)
NH2-Gly-Leu-Arg-Ile-Leu-Leu-Leu-Lys-Val-OH;

(SEQ. ID. NO. 2)
NH2-Leu-Lys-Ile-Leu-Leu-Leu-Arg-Val-OH;

(SEQ. ID. NO. 3)
NH2-Gly-Phe-Arg-Ile-Leu-Leu-Leu-Lys-Val-OH;

(SEQ. ID. NO. 4)
NH2-Val-Phe-Arg-Ile-Leu-Leu-Leu-Lys-Val-OH;

(SEQ. ID. NO. 5)
NH2-Phe-Lys-Ile-Leu-Leu-Leu-Arg-Val-OH;

(SEQ. ID. NO. 6)
NH2-Ala-Arg-Leu-Pro-Val-Leu-Lys-Leu-Val-OH;

(SEQ. ID. NO. 7)
NH2-Arg-Val-Met-Ala-Pro-Arg-Ala-Leu-Leu-OH;

(SEQ. ID. NO. 8)
NH2-Val-Lys-Leu-Phe-Pro-Val-Lys-Leu-Phe-Pro-OH;

(SEQ. ID. NO. 9)
NH2-Leu-Arg-Ile-Leu-Leu-Leu-Ile-Lys-Val-OH;

(SEQ. ID. NO. 10)
NH2-Leu-Arg-Leu-Leu-Leu-Lys-Val-OH;

(SEQ. ID. NO. 11)
NH2-Met-Gly-Leu-Arg-Ile-Leu-Leu-Leu-OH;

(SEQ. ID. NO. 12)
NH2-Leu-Asp-Ile-Leu-Leu-Leu-Glu-Val-OH;

(SEQ. ID. NO. 13)
NH2-Ile-Leu-Leu-Leu-Lys-Val-Ala-Gly-Phe-OH;

(SEQ. ID. NO. 14)
NH2-Ile-Leu-Leu-Leu-Lys-Val-Ala-Gly-OH;

(SEQ. ID. NO. 15)
NH2-Leu-Arg-Ile-Leu-Leu-Leu-Gly-Val-OH;

(SEQ. ID. NO. 16)
NH2-Leu-Gly-Ile-Leu-Leu-Leu-Lys-Val-OH;

(SEQ. ID. NO. 17)
NH2-Ile-Leu-Leu-Gly-Lys-Ala-Thr-Leu-Tyr-OH;

(SEQ. ID. NO. 18)
NH2-Leu-Leu-Met-Thr-Leu-Arg-Leu-Trp-Ser-Ser-OH;

(SEQ. ID. NO. 19)
NH2-Ile-Ile-Val-Thr-Asp-Val-Ile-Ala-Thr-Leu-OH;

(SEQ. ID. NO. 20)
NH2-Ile-Val-Ile-Val-Asp-Ile-Cys-Ile-Thr-OH;

(SEQ. ID. NO. 21)
NH2-Phe-Leu-Phe-Ala-Glu-Ile-Val-Ser-Ile-OH;

(SEQ. ID. NO. 22)
NH2-Tyr-Gly-Arg-Ala-Asp-Cys-Gly-Ile-Thr-Ser-OH;

(SEQ. ID. NO. 23)
NH2-Trp-Gly-Arg-Ala-Asp-Cys-Gly-Ile-Thr-Ser-OH;

(SEQ. ID. NO. 24)
NH2-Tyr-Gly-Arg-Ala-Asp-Cys-Ile-Thr-Ser-OH;
and (SEQ. ID. NO. 25)
NH2-Ser-Ser-Asp-Val-Pro-Cys-Asp-Ala-Thr-Leu-Thr-OH;
``` wherein the C-terminus of said peptide is conjugated to a lipid moiety selected from: N-palmitoyl-S-[2,3-bis(palmitoyloxy) propyl]cysteine (Pam3Cys), or an analogue thereof in which only two acyl substituents are present.

6. A method according to claim 1, in which the inflammatory airway or lung disease is asthma.

7. A method according to claim 1, in which the inflammatory airway or lung disease is chronic obstructive pulmonary disease.

8. A method according to claim 1, in which the peptide is administered intravenously, subcutaneously, intratracheally, intrabronchially, intranasally or via inhalation.

9. A method according to claim 8, in which the peptide is administered via inhalation.

10. A method according to claim 9, in which the peptide is administered utilising an aerosol, nebuliser or dry powder inhalation device.

11. A composition comprising a peptide selected from the group consisting of:

```
                                           (SEQ. ID. NO. 1)
NH2-Gly-Leu-Arg-Ile-Leu-Leu-Leu-Lys-Val-OH;

(SEQ. ID. NO. 2)
NH2-Leu-Lys-Ile-Leu-Leu-Leu-Arg-Val-OH;

(SEQ. ID. NO. 3)
NH2-Gly-Phe-Arg-Ile-Leu-Leu-Leu-Lys-Val-OH;

(SEQ. ID. NO. 4)
NH2-Val-Phe-Arg-Ile-Leu-Leu-Leu-Lys-Val-OH;

(SEQ. ID. NO. 5)
NH2-Phe-Lys-Ile-Leu-Leu-Leu-Arg-Val-OH;

(SEQ. ID. NO. 6)
NH2-Ala-Arg-Leu-Pro-Val-Leu-Lys-Leu-Val-OH;

(SEQ. ID. NO. 7)
NH2-Arg-Val-Met-Ala-Pro-Arg-Ala-Leu-Leu-OH;

(SEQ. ID. NO. 8)
NH2-Val-Lys-Leu-Phe-Pro-Val-Lys-Leu-Phe-Pro-OH;

(SEQ. ID. NO. 9)
NH2-Leu-Arg-Ile-Leu-Leu-Leu-Ile-Lys-Val-OH;

(SEQ. ID. NO. 10)
NH2-Leu-Arg-Leu-Leu-Leu-Lys-Val-OH;

(SEQ. ID. NO. 11)
NH2-Met-Gly-Leu-Arg-Ile-Leu-Leu-Leu-OH;

(SEQ. ID. NO. 12)
NH2-Leu-Asp-Ile-Leu-Leu-Leu-Glu-Val-OH;

(SEQ. ID. NO. 13)
NH2-Ile-Leu-Leu-Leu-Lys-Val-Ala-Gly-Phe-OH;

(SEQ. ID. NO. 14)
NH2-Ile-Leu-Leu-Leu-Lys-Val-Ala-Gly-OH;

(SEQ. ID. NO. 15)
NH2-Leu-Arg-Ile-Leu-Leu-Leu-Gly-Val-OH;

(SEQ. ID. NO. 16)
NH2-Leu-Gly-Ile-Leu-Leu-Leu-Lys-Val-OH;

(SEQ. ID. NO. 17)
NH2-Ile-Leu-Leu-Gly-Lys-Ala-Thr-Leu-Tyr-OH;

(SEQ. ID. NO. 18)
NH2-Leu-Leu-Met-Thr-Leu-Arg-Leu-Trp-Ser-Ser-OH;

(SEQ. ID. NO. 19)
NH2-Ile-Ile-Val-Thr-Asp-Val-Ile-Ala-Thr-Leu-OH;

(SEQ. ID. NO. 20)
NH2-Ile-Val-Ile-Val-Asp-Ile-Cys-Ile-Thr-OH;

(SEQ. ID. NO. 21)
NH2-Phe-Leu-Phe-Ala-Glu-Ile-Val-Ser-Ile-OH;

(SEQ. ID. NO. 22)
NH2-Tyr-Gly-Arg-Ala-Asp-Cys-Gly-Ile-Thr-Ser-OH;

(SEQ. ID. NO. 23)
NH2-Trp-Gly-Arg-Ala-Asp-Cys-Gly-Ile-Thr-Ser-OH;

(SEQ. ID. NO. 24)
NH2-Tyr-Gly-Arg-Ala-Asp-Cys-Ile-Thr-Ser-OH;
and
                                           (SEQ. ID. NO. 25)
NH2-Ser-Ser-Asp-Val-Pro-Cys-Asp-Ala-Thr-Leu-Thr-OH;
``` wherein the C-terminus of said peptide is conjugated to a lipid moiety selected from: N-palmitoyl-S-[2,3-bis(palmitoyloxy)propyl]cysteine (Pam3Cys), or an analogue thereof in which only two acyl substituents are present.

12. A composition according to claim 11, which is in ready-to-administer form in a sealed vial, container or cartridge.

13. A composition according to claim 11, in which the composition is sterile.

14. A composition according to claim 11, in which the composition comprises a stabilizer and/or a bulking agent.

15. A composition according to claim 12, in which the composition is suitable for delivery by inhalation, and in which the sealed vial, container or cartridge is an inhalation device adapted to deliver the composition to a patient via inhalation.

16. A composition according to claim 15, in which the inhalation device comprises an aerosol, nebuliser or dry powder delivery mechanism.

17. A composition according to claim 15, in which the inhalation device comprises an aerosol.

18. A composition according to claim 15, in which the inhalation device delivers the composition in dry powder form.

19. A composition according to claim 15, in which the inhalation device comprises a nebuliser.

20. A composition according to claim 11, in which the composition does not require reconstitution before use.

21. An article of manufacture, comprising a peptide selected from the group consisting of:

```
                                           (SEQ. ID. NO. 1)
NH2-Gly-Leu-Arg-Ile-Leu-Leu-Leu-Lys-Val-OH;

(SEQ. ID. NO. 2)
NH2-Leu-Lys-Ile-Leu-Leu-Leu-Arg-Val-OH;

(SEQ. ID. NO. 3)
NH2-Gly-Phe-Arg-Ile-Leu-Leu-Leu-Lys-Val-OH;

(SEQ. ID. NO. 4)
NH2-Val-Phe-Arg-Ile-Leu-Leu-Leu-Lys-Val-OH;

(SEQ. ID. NO. 5)
NH2-Phe-Lys-Ile-Leu-Leu-Leu-Arg-Val-OH;

(SEQ. ID. NO. 6)
NH2-Ala-Arg-Leu-Pro-Val-Leu-Lys-Leu-Val-OH;

(SEQ. ID. NO. 7)
NH2-Arg-Val-Met-Ala-Pro-Arg-Ala-Leu-Leu-OH;

(SEQ. ID. NO. 8)
NH2-Val-Lys-Leu-Phe-Pro-Val-Lys-Leu-Phe-Pro-OH;

(SEQ. ID. NO. 9)
NH2-Leu-Arg-Ile-Leu-Leu-Leu-Ile-Lys-Val-OH;
```

-continued

NH$_2$-Leu-Arg-Leu-Leu-Leu-Lys-Val-OH; (SEQ. ID. NO. 10)

NH$_2$-Met-Gly-Leu-Arg-Ile-Leu-Leu-Leu-OH; (SEQ. ID. NO. 11)

NH$_2$-Leu-Asp-Ile-Leu-Leu-Leu-Glu-Val-OH; (SEQ. ID. NO. 12)

NH$_2$-Ile-Leu-Leu-Leu-Lys-Val-Ala-Gly-Phe-OH; (SEQ. ID. NO. 13)

NH$_2$-Ile-Leu-Leu-Leu-Lys-Val-Ala-Gly-OH; (SEQ. ID. NO. 14)

NH$_2$-Leu-Arg-Ile-Leu-Leu-Leu-Gly-Val-OH; (SEQ. ID. NO. 15)

NH$_2$-Leu-Gly-Ile-Leu-Leu-Leu-Lys-Val-OH; (SEQ. ID. NO. 16)

NH$_2$-Ile-Leu-Leu-Gly-Lys-Ala-Thr-Leu-Tyr-OH; (SEQ. ID. NO. 17)

NH$_2$-Leu-Leu-Met-Thr-Leu-Arg-Leu-Trp-Ser-Ser-OH; (SEQ. ID. NO. 18)

NH$_2$-Ile-Ile-Val-Thr-Asp-Val-Ile-Ala-Thr-Leu-OH; (SEQ. ID. NO. 19)

NH$_2$-Ile-Val-Ile-Val-Asp-Ile-Cys-Ile-Thr-OH; (SEQ. ID. NO. 20)

NH$_2$-Phe-Leu-Phe-Ala-Glu-Ile-Val-Ser-Ile-OH; (SEQ. ID. NO. 21)

NH$_2$-Tyr-Gly-Arg-Ala-Asp-Cys-Gly-Ile-Thr-Ser-OH; (SEQ. ID. NO. 22)

NH$_2$-Trp-Gly-Arg-Ala-Asp-Cys-Gly-Ile-Thr-Ser-OH; (SEQ. ID. NO. 23)

NH$_2$-Tyr-Gly-Arg-Ala-Asp-Cys-Ile-Thr-Ser-OH; (SEQ. ID. NO. 24)
and

NH$_2$-Ser-Ser-Asp-Val-Pro-Cys-Asp-Ala-Thr-Leu-Thr-OH; (SEQ. ID. NO. 25)

wherein the C-terminus of said peptide is conjugated to a lipid moiety selected from: N-palmitoyl-S-[2,3-bis(palmitoyloxy) propyl]cysteine (Pam3Cys), or an analogue thereof in which only two acyl substituents are present together with a pharmaceutically acceptable carrier, in a dosage form suitable for administration by a patient.

22. An article of manufacture according to claim 21, in which the dosage form is labeled with, or accompanied by, instructions for treating or preventing inflammatory airway or lung disease in a human.

23. An article of manufacture according to claim 21, which is a sealed vial, container or cartridge containing a ready-to-administer composition.

24. An article of manufacture according to claim 21, in which the article of manufacture is a sterile composition.

25. An article of manufacture according to claim 21, in which the article of manufacture is a composition comprising a stabilizer and/or a bulking agent.

26. An article of manufacture according to claim 23, in which the sealed vial, container or cartridge is an inhalation device adapted to deliver the composition to the patient via inhalation.

27. An article of manufacture according to claim 26, in which the inhalation device comprises an aerosol.

28. An article of manufacture according to claim 26, in which the inhalation device delivers the composition in dry powder form.

29. An article of manufacture according to claim 26, in which the inhalation device comprises a nebuliser.

30. An article of manufacture according to claim 21, in which the article of manufacture is a composition that does not require reconstitution before use.

31. An article of manufacture according to claim 21, further comprising said peptide in a dosage form suitable for administration to a patient with asthma.

32. An article of manufacture according to claim 21, further comprising said peptide in a dosage form suitable for administration to a patient suffering from chronic obstructive pulmonary disease.

* * * * *

SEQUENCE LISTING

```
<160> NUMBER OF SEQ ID NOS: 40

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Leu Arg Ile Leu Leu Leu Lys Val
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

```
Leu Lys Ile Leu Leu Leu Arg Val
  1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Phe Arg Ile Leu Leu Leu Lys Val
  1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Phe Arg Ile Leu Leu Leu Lys Val
  1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Lys Ile Leu Leu Leu Arg Val
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Arg Leu Pro Val Leu Lys Leu Val
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Val Met Ala Pro Arg Ala Leu Leu
  1               5

<210> SEQ ID NO 8
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 8

Val Lys Leu Phe Pro Val Lys Leu Phe Pro
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Arg Ile Leu Leu Leu Ile Lys Val
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Arg Leu Leu Leu Lys Val
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Gly Leu Arg Ile Leu Leu Leu
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Asp Ile Leu Leu Leu Glu Val
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Leu Leu Leu Lys Val Ala Gly Phe
1               5
```

-continued

```
<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Leu Leu Leu Lys Val Ala Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Arg Ile Leu Leu Leu Gly Val
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Gly Ile Leu Leu Leu Lys Val
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Leu Leu Gly Lys Ala Thr Leu Tyr
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Leu Met Thr Leu Arg Leu Trp Ser Ser
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 19

Ile Ile Val Thr Asp Val Ile Ala Thr Leu
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Val Ile Val Asp Ile Cys Ile Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Leu Phe Ala Glu Ile Val Ser Ile
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Gly Arg Ala Asp Cys Gly Ile Thr Ser
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Gly Arg Ala Asp Cys Gly Ile Thr Ser
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Gly Arg Ala Asp Cys Ile Thr Ser
1               5

<210> SEQ ID NO 25
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 25

Ser Ser Asp Val Pro Cys Asp Ala Thr Leu Thr
1               5                   10

<210> SEQ ID NO 26
<211> LENGTH: 9
<212> TYPE: PRT
<213> ORGANISM: Homo sapiens

<400> SEQUENCE: 26

Gly Phe Arg Ile Leu Leu Leu Lys Val
1               5

<210> SEQ ID NO 27
<211> LENGTH: 9
<212> TYPE: PRT
<213> ORGANISM: Mus sp.

<400> SEQUENCE: 27

Gly Leu Arg Ile Leu Leu Leu Lys Val
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Leu Arg Ile Leu Leu Leu Leu Lys Val
1               5                   10

<210> SEQ ID NO 29
<211> LENGTH: 23
<212> TYPE: PRT
<213> ORGANISM: Mus sp.

<400> SEQUENCE: 29

Asn Leu Ser Val Met Gly Leu Arg Ile Leu Leu Leu Lys Val Ala Gly
1               5                   10                  15

Phe Asn Leu Leu Met Thr Leu
            20

<210> SEQ ID NO 30
<211> LENGTH: 23
<212> TYPE: PRT
<213> ORGANISM: Rattus sp.

<400> SEQUENCE: 30

Asn Leu Ser Val Met Gly Leu Arg Ile Leu Leu Leu Lys Val Ala Gly
1               5                   10                  15

Phe Asn Leu Leu Met Thr Leu
            20

<210> SEQ ID NO 31
<211> LENGTH: 23
<212> TYPE: PRT
<213> ORGANISM: Ovis sp.
```

-continued

```
<400> SEQUENCE: 31

Asn Leu Ser Val Thr Val Phe Arg Ile Leu Leu Leu Lys Val Val Gly
 1               5                  10                  15

Phe Asn Leu Leu Met Thr Leu
            20

<210> SEQ ID NO 32
<211> LENGTH: 23
<212> TYPE: PRT
<213> ORGANISM: Bos sp.

<400> SEQUENCE: 32

Asn Leu Ser Val Ile Val Phe Arg Ile Leu Leu Leu Lys Val Val Gly
 1               5                  10                  15

Phe Asn Leu Leu Met Thr Leu
            20

<210> SEQ ID NO 33
<211> LENGTH: 23
<212> TYPE: PRT
<213> ORGANISM: Homo sapiens

<400> SEQUENCE: 33

Asn Leu Ser Val Ile Gly Phe Arg Ile Leu Leu Leu Lys Val Ala Gly
 1               5                  10                  15

Phe Asn Leu Leu Met Thr Leu
            20

<210> SEQ ID NO 34
<211> LENGTH: 28
<212> TYPE: PRT
<213> ORGANISM: Mus sp.

<400> SEQUENCE: 34

Asn Leu Ser Val Met Gly Leu Arg Ile Leu Leu Leu Lys Val Ala Gly
 1               5                  10                  15

Phe Asn Leu Leu Met Thr Leu Arg Leu Trp Ser Ser
            20                  25

<210> SEQ ID NO 35
<211> LENGTH: 23
<212> TYPE: PRT
<213> ORGANISM: Homo sapiens

<400> SEQUENCE: 35

Asn Leu Ser Val Ile Gly Phe Arg Ile Leu Leu Leu Lys Val Ala Gly
 1               5                  10                  15

Phe Asn Leu Leu Met Thr Leu
            20

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Gly Ile Leu Leu Leu Gly Val
 1               5
```

```
<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Arg Ile Leu Leu Leu Ile Lys Val
 1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ile Leu Leu Leu Lys Val
 1               5

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Gly Arg Ala Asp Gly Gly Ile Thr Ser
 1               5                  10

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Gly Phe Asn Leu Leu Met Thr
 1               5
```